US009675292B2

(12) United States Patent
Fadem

(10) Patent No.: US 9,675,292 B2
(45) Date of Patent: Jun. 13, 2017

(54) EVOKED RESPONSE TESTING SYSTEM FOR NEUROLOGICAL DISORDERS

(71) Applicant: Neuronetrix Solutions, LLC, Louisville, KY (US)

(72) Inventor: Kalford C. Fadem, Louisville, KY (US)

(73) Assignee: Neuronetrix, Inc., Louisville, KY (US)

( * ) Notice: Subject to any disclaimer, the term of this patent is extended or adjusted under 35 U.S.C. 154(b) by 0 days.

(21) Appl. No.: 14/152,207

(22) Filed: Jan. 10, 2014

(65) Prior Publication Data

US 2014/0128763 A1 May 8, 2014

Related U.S. Application Data

(63) Continuation of application No. 11/570,630, filed as application No. PCT/US2005/021272 on Jun. 16, 2005, now abandoned.
(Continued)

(51) Int. Cl.
*A61B 5/04* (2006.01)
*A61B 5/16* (2006.01)
(Continued)

(52) U.S. Cl.
CPC .............. *A61B 5/16* (2013.01); *A61B 5/0002* (2013.01); *A61B 5/0478* (2013.01);
(Continued)

(58) Field of Classification Search
CPC ............................ A61B 5/0476; A61B 5/0482
(Continued)

(56) References Cited

U.S. PATENT DOCUMENTS

| 4,412,547 A | 11/1983 | Callahan et al. |
| 4,677,604 A | 6/1987 | Selby, III et al. |

(Continued)

FOREIGN PATENT DOCUMENTS

| AU | 745602 B2 | 3/2002 |
| AU | 2011244986 B2 | 11/2002 |

(Continued)

OTHER PUBLICATIONS

Price, The Effect of Pre-Stimulus Alpha Activity on the Auditory P300 Paradigm: A Prospective Study, Brain Topography, vol. 9, No. 3, 1997, pp. 169-175.*

(Continued)

*Primary Examiner* — Michael Kahelin
*Assistant Examiner* — Tho Tran
(74) *Attorney, Agent, or Firm* — Frost Brown Todd LLC

(57) ABSTRACT

A dyslexia screening system suitable for clinical use includes an integrated headset that efficiently and conveniently performs an auditory evoked response (ERP) test by positioning electrodes about the ears of the subject. An integral control module automatically performs the test, providing simplified controls and indications to the clinician. A number of screening tests that are stored in the headset are periodically uploaded for billing, remote analysis and result reporting. A paradigm that characterizes testing performed for a subject along with the patient identification and/or patient demographics are stored in an associated fashion for later fusion and analyses with similar but not necessarily identically constructed ERP tests.

20 Claims, 25 Drawing Sheets

Related U.S. Application Data

(60) Provisional application No. 60/580,853, filed on Jun. 18, 2004.

(51) Int. Cl.
*A61B 5/00* (2006.01)
*A61B 5/0478* (2006.01)
*A61B 5/0484* (2006.01)

(52) U.S. Cl.
CPC ...... *A61B 5/04842* (2013.01); *A61B 5/04845* (2013.01); *A61B 5/6814* (2013.01); *A61B 2560/045* (2013.01); *A61B 2562/08* (2013.01)

(58) Field of Classification Search
USPC .................................................. 600/544, 545
See application file for complete search history.

(56) References Cited

U.S. PATENT DOCUMENTS

| | | | |
|---|---|---|---|
| 4,987,903 | A | 1/1991 | Keppel et al. |
| 5,269,302 | A | 12/1993 | Swartz et al. |
| 5,320,109 | A | 6/1994 | Chamoun et al. |
| 5,406,956 | A | 4/1995 | Farwell |
| 5,730,146 | A | 3/1998 | Itil et al. |
| 5,740,812 | A * | 4/1998 | Cowan ............... A61B 5/04845 600/545 |
| 6,052,619 | A | 4/2000 | John |
| 6,231,187 | B1 * | 5/2001 | Munoz et al. ................ 351/209 |
| 6,360,122 | B1 | 3/2002 | Fischell et al. |
| 6,597,954 | B1 | 7/2003 | Fischell et al. |
| 6,654,626 | B2 | 11/2003 | Devlin et al. |
| 2001/0028309 | A1 * | 10/2001 | Torch ............................ 340/575 |
| 2001/0039385 | A1 * | 11/2001 | Ellenz ................ A61B 5/0006 600/524 |
| 2002/0188216 | A1 * | 12/2002 | Kayyali et al. ............... 600/544 |
| 2004/0015894 | A1 | 1/2004 | Lange |
| 2004/0019259 | A1 | 1/2004 | Brown et al. |
| 2004/0092809 | A1 | 5/2004 | DeCharms |
| 2004/0097839 | A1 | 5/2004 | Epley |
| 2004/0225179 | A1 * | 11/2004 | Kaplan et al. .................. 600/26 |

FOREIGN PATENT DOCUMENTS

| | | |
|---|---|---|
| AU | 2005265033 B2 | 8/2011 |
| AU | 2013200921 A1 | 3/2013 |
| EP | 1 275 340 A1 | 1/2003 |
| EP | 2 260 760 A1 | 12/2010 |
| JP | 4833202 B2 | 12/2011 |
| WO | WO 99/59469 | 11/1999 |
| WO | WO 02/089667 | 11/2002 |
| WO | WO 02/100267 | 12/2002 |
| WO | WO 2004/112604 | 12/2004 |
| WO | WO 2005/010515 | 2/2005 |
| WO | WO 2006/009771 | 1/2006 |

OTHER PUBLICATIONS

Fonaryova Key, A.P., et al., "Linking Brainwaves to the Brain: An ERP Primer," Developmental Neuropsychology, 27(2), 2005, pp. 183-215.
International Search Report and Written Opinion dated Oct. 17, 2005 for Application No. PCT/US2005/021272.
European Search Report and Written Opinion dated Oct. 22, 2010 for Application No. EP 10182359.
EP Communication dated Jun. 18, 2008 for Application No. EP 05 766 097.9.
EP Communication dated Aug. 6, 2007 for Application No. EP 05 766 097.9.
Australian Office Action dated Mar. 16, 2010 for Application No. AU 2005265033.
U.S. Appl. No. 11/570,630, filed May 8, 2007.
U.S. Appl. No. 60/580,772, filed Jun. 18, 2004.
U.S. Appl. No. 60/580,853, filed Jun. 18, 2004.
Australian Office Action dated Nov. 11, 2010 for Application No. AU 2005265033, 3 pgs.
Australian Office Action dated Jun. 4, 2012 for Application No. AU 2011244986, 2 pgs.
Australian Office Action dated Oct. 11, 2013 for Application No. AU 2013200921, 3 pgs.
Australian Office Action dated Oct. 18, 2013 for Application No. AU 2013200921, 3 pgs.
Australian Office Action dated Dec. 7, 2015 for Application No. AU 2014240373, 3 pgs.
EP Communication dated Feb. 25, 2014 for Application No. EP 5766097.9, 7 pgs.
EP Communication dated Sep. 24, 2014 for Application No. EP 5766097.9, 5 pgs.
EP Communication dated Jan. 29, 2016 for Application No. EP 5766097.9, 3 pgs.
Japanese Office Action dated Apr. 25, 2011 for Application No. JP 2007-516729, 6 pgs.
The Newbie Club, Download Mysteries Solved, Oct. 1, 2003 accessed from: http://web.archive.org/web/20031001212148/http://newbieclub.com/download/, 6 pgs.

* cited by examiner

| Auditory Stimulus Library ||| 
|---|---|---|
| Click |  | Narrow band spike |
| Burst |  | Broadband short duration |
| Pip/Chirp |  | Single frequency half-cycle carrier |
| Steady-State Tone |  | Single frequency constant amplitude |
| MASTER |  | Single frequency continuous cycles |
| Phoneme |  | Single-phoneme speech sound |
| Word | 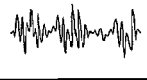 | Word |
FIG. 10

| Sequence Library | |
|---|---|
| Repetition | Repeat single stimuli |
| Steady-State | Single tone w/long duration |
| Equal Probability | Multiple stimuli with each repeated an equal number of times |
| Match-Mismatch | A pair of stimuli, presented with minimal interstimulus delay, which either match or do not match |
| Oddball | A single standard stimuli w/one or more deviant stimuli |
| Variable Frequency | Constant volume, vary frequency |
| Variable Volume | Constant frequency, vary volume |
| Variable Time Warp | Constant tone, vary duration |
| User Defined | User defined sequence presentation, volume, tone, and time warp |

FIG. 11

| Data Capture Settings ||
|---|---|
| Electrode Location | Location I.D. using 10-20 system |
| Electrode Selection | Which electrodes will be selected for data capture |
| Data Capture Start-End | When should the data capture begin and end |
| Data Capture Rate | What rate should the system sample the electrodes to capture data |
| Signal Gain | Signal amplification |
| Artifact Threshold | Voltage threshold to be used to instruct the system when to replay the stimulus set |

FIG. 12

"Oddball"

a - a - a - a - b - a - a - a - b - a - a - a - a - c

⟵ Set 1 ⟶   ⟵ Set 2 ⟶   ⟵ Set 3 ⟶

"Match-Mismatch"

a - b - a - a - b - a - b - b

⟷ ⟷ ⟷ ⟷
Set 1 Set 2 Set 3 Set 4

"Equal Probability (block random grouping)"

a - b - c - d - c - a - d - b - b - d - a - c

⟵ Set 1 ⟶   ⟵ Set 2 ⟶   ⟵ Set 3 ⟶

FIG. 14

FIG. 17
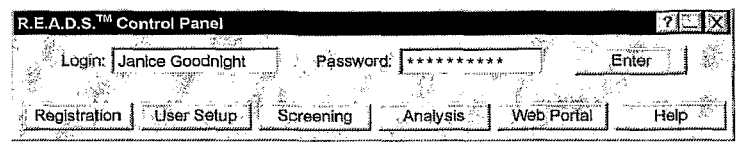
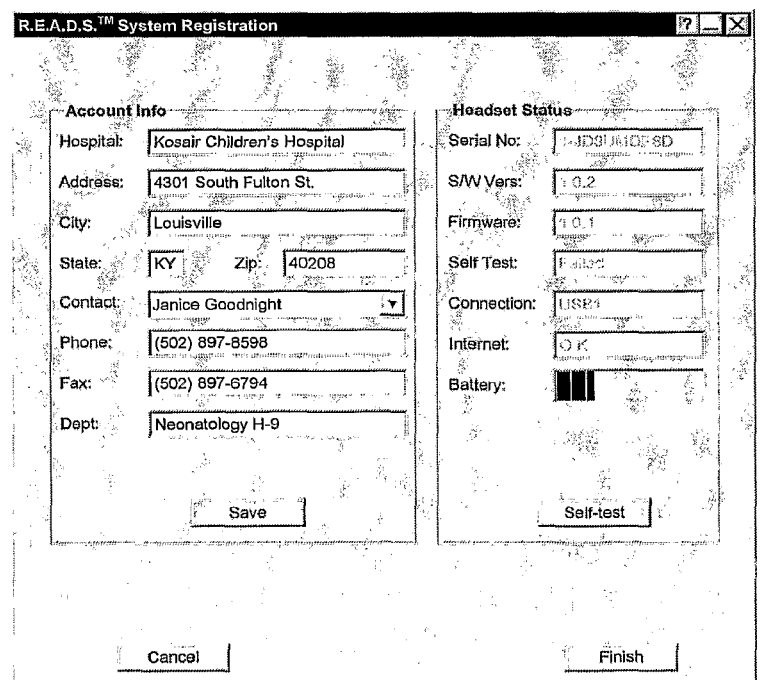
FIG. 18

| R.E.A.D.S.™ Screening | | | | | | | |
|---|---|---|---|---|---|---|---|
| Protocol Setup | Data Upload | | | | | | |
| Enter text | | | | | | | |
| Test | Patient ID | Mother's Name | Birthday | Sex | Weight | Record | Status |
| 1 | 129850895 | Ethyl Johnson | 06/26/03 | M | 12lb 14oz | 9JHY86J7 | Pass |
| 2 | 129630622 | Lavern Miller | 06/27/03 | F | 9lb 8oz | 9GU74K8 | Max |
| 3 | | | | | | | |
| 4 | | | | | | | |
| 5 | | | | | | | |
| 6 | | | | | | | |
| 7 | | | | | | | |
| 8 | | | | | | | |
| 9 | | | | | | | |
| 10 | | | | | | | |

Cancel  Load EMR  Save  Finish

FIG. 23

EVOKED RESPONSE TESTING SYSTEM FOR NEUROLOGICAL DISORDERS

The present application is a continuation of U.S. patent application Ser. No. 11/570,630, entitled "Evoked Response Testing System for Neurological Disorders," filed May 8, 2007, the disclosure of which is incorporated herein, and which is a National Stage Entry of PCT International Patent App. No. PCT/US05/021272, entitled "Evoked Response Testing System for Neurological Disorders," filed Jun. 16, 2005, the disclosure of which is incorporated by reference herein, which in turn claims the benefit of U.S. Patent App. No. 60/580,853, entitled "Auditory Evoked Response Mapping System for Auditory Neurome," filed Jun. 18, 2004, the disclosure of which is incorporated by reference herein.

Subject matter disclosed in the present application is also related to subject matter disclosed in PCT International Patent App. No. PCT/US05/021257, entitled "Wireless Electrode for Biopotential Measurement," filed Jun. 16, 2005, the disclosure of which is incorporated by reference herein, and which in turn claims the benefit of U.S. Patent App. No. 60/580,772, entitled "Wireless Electrode for Biopotential Measurement," filed Jun. 18, 2004.

FIELD OF THE INVENTION

The present invention relates generally to a method and apparatus for capturing electroencephalogram (EEG) signals. More particularly, the present invention provides a method and describes a system for the purpose of diagnosing dyslexia, and similar neurological disorders such as autism, schizophrenia, Alzheimer's etc., by capturing brain waves produced while processing a preprogrammed auditory or visual stimulus.

BACKGROUND OF THE INVENTION

As described in the cross-referenced PCT application, EEG measurements from auditory evoked responses (AER) or visual evoked responses (VER) detect voltage potentials from the brain as the brain processes the specific stimulus or sequence of stimuli. The pattern of EEG signals evoked in this way are called Evoked Response Potentials (ERPs). Specific combinations, sequences and timing of various stimuli which evoke an identifiable EEG response based on known neural processes are called ERP paradigms. Various ERP paradigms are used to evoke EEG responses that can be correlated with neurological disorders. ERPs from dyslexic children often show abnormally high peak voltages and long signal latencies. These characteristics may correlate to higher than normal energy requirements to process sounds and slower discrimination and sound-to-symbol mapping, the outward manifestations of which will primarily be difficulty in reading and writing.

With regard to these broader applications, research has increasingly sought greater insight into brainwaves, such as overviewed in "LINKING BRAINWAVES TO THE BRAIN: AN ERP PRIMER" by Alexandra P. Fonaryova Key, Guy O. Dove, and Mandy J. Maguire. Over the latter portion of the past century recordings of brain electrical activity such as the continuous electroencephalogram (EEG) and the stimulus- or task-relevant event-related potentials became frequent tools of choice for investigating the brain's role in cognitive processing and neurological disorders. Electrophysiological recording techniques are generally non-invasive, relatively inexpensive, and do not require that participants provide a motor or verbal response. Furthermore, virtually identical procedures can be used across the entire life span. While the ongoing EEG reflects a wide-range of neural activity related to the various sensory and cognitive functions, it is also affected by the myriad of self-regulation processes (e.g., maintaining temperature, heart rate, breathing) ongoing in the brain at the same time. This intermixing of signals makes it difficult to separate cognitive and physiological contributors to the observed EEG. By contrast, the ERP approach permits investigators to more directly link stimulus events to the recorded signal. The ERP is a portion of the EEG that is time-locked to the precise onset (or in some cases offset) of the stimulus presentation (e.g., sound or visual stimulus). Analyses generally focus on the change in the electrophysiological signal that immediately follows the stimulus event enabling researchers to evaluate the relationship between the neuroelectrical response and the stimulus. The ERP signal that is finally detected at the scalp is not an exact and completely stable pattern that reflects only those discrete neural events directly related to the evoking stimulus, the task, or the subject's state. The smaller size of the ERP relative to other physiological events can also make it difficult to discern the relevant signal. To accommodate these factors, researchers employ repeated presentations of the evoking stimulus to average out potentially unrelated events (those signals which are not time-locked to the stimulus).

ERPs have been successfully used to study both general and specific aspects of an individual's response to events in the external as well as internal environment. Neuropsychological research of cognitive functioning in various populations also demonstrated that ERP components could serve as informative markers of neurodevelopmental status in general as well as the development of more specific abilities. Additional advantages of the ERP technique over other neuroimaging procedures include (1) very fine temporal resolution (on the order of milliseconds or even fractions of a millisecond) that reveals even momentary changes in patterns of brain activation that otherwise could go unnoticed, and (2) relatively gross level spatial resolution capabilities that permit a basis for theorizing about the distribution of brain mechanisms that subserve these cognitive functions.

The ERP is generally believed to reflect post-synaptic (dendritic) potentials of a fairly extensive set of neurons activated in close temporal proximity. However, information recorded at the scalp cannot capture all of the generated electrical activity. Signals that originate within the brain must travel through a variety of tissues of different densities and resistances (e.g., neurons, fiber tracts, cerebral spinal fluid, skull) before reaching the recording electrode on the scalp. It may be difficult to detect a signal if the distance from the cortical or subcortical regions generating the signal to the scalp is too great relative to the signal's strength. In addition, the orientation of the cortical columns generating the signal may affect whether a signal reaches the scalp. If the columns are perpendicular to the scalp and signal strength is sufficient, the likelihood of the electrode detecting the signal is good. On the other hand, if the cell columns are oriented parallel to the scalp or at some other angle to it, the signal may project to an area away from the nearest electrode above it or not project to the scalp at all.

ERP waveforms are often described in terms of positive and negative peaks (i.e., the most positive and negative deflections in the wave). At a general level, the labeling can refer to the sequence in which the peak occurs while at the same time indicating its polarity. For example, "N1" would refer to the first negative going peak in the waveform while "N2" would refer to the second negative occurring peak. Likewise, "P1" refers to the first positive deflection or peak in the ERP waveform while "P2" refers to the second positive peak. The naming scheme for ERP components can also identify the positive and negative peaks by their latency (usually defined as the time from stimulus onset). "N100" in this example refers to the negative peak that occurs 100 ms following stimulus onset. "P300" would identify the positive peak that occurred 300 ms post stimulus onset.

Recently, it has been recognized that a comprehensive evaluation of the EEG producing mechanisms within the brain would have significant advantages, specifically the four ERP characteristics: peak latency, cognitive functional significance, cortical distributions, and component brain sources. For the purpose of consistency and clarity, the peaks are generally identified by their polarity (which itself can vary as a function of stimulus modality and reference location) and place in the sequence of components rather than by exact latency due to possible variations in the latter due to developmental, environmental, or clinical effects (unless the latency is the predominant descriptor of the peak).

Challenges exist for a comprehensive approach to detection and analysis due to generally-known techniques for source localization that rely on different principles which can produce conflicting results. Thus, findings from intracranial recordings, functional magnetic resonance imaging (fMRI), magnetoencephalography (MEG), brain electromagnetic source analysis (BESA), positron emission tomography (PET), or low-resolution brain electromagnetic tomography (LORETA) may not always agree.

In addition, there are a large number of ERP peaks to detect and analyze characterized by peak amplitude and latency effects, scalp distributions and neural substrates. These include P1, N1, P2, N2, Mismatch negativity (MMN), P3a, P3b, N400, and P600. This list is not assumed to be exhaustive. Other ERP components such as the Contingent Negative Variation, the Left Anterior Negativity, the Late Positive Potential, and the Positive Slow Wave are not included in the current review due to a sparcity of information regarding their sources and/or the limited space available to cover a large amount of research.

The P1 peak is not always easily identified, but when present, occurs approximately 50 ms after an auditory stimulus onset (also known as P50) or about 100 ms after the onset of a visual stimulus. Functionally this component is typically interpreted as a neurophysiological indicator of preferential attention to sensory inputs. The auditory P1 appears earlier in time (shorter latency) over posterior scalp electrode sites but with larger amplitudes over frontal and/or central regions. It has been reported that P50 response was largest over the Cz electrode. The distribution is symmetrical over the two hemispheres except for the anterior temporal regions where larger amplitudes are noted over the left hemisphere. Overall, peak amplitude and latency appears to decrease with age to the point where the peak disappears.

Auditory P1 has been frequently associated with auditory inhibition in a sensory gating paradigm where paired clicks are presented at relatively short inter-stimulus intervals. The amplitude of the averaged ERP to the second of the paired clicks is typically reduced compared to the averaged response to the first click. The magnitude of this suppression is commonly interpreted as a neurophysiological index of sensory gating. Reduced suppression is frequently reported for schizophrenic patients. However in certain neuropsychiatric disorders, including mania and schizophrenia, peak amplitude to paired stimuli is reported to be approximately equal. P1 latency is frequently used clinically to diagnose neurodegenerative diseases, such as multiple sclerosis and Parkinson's disease.

It has been proposed that the P50 response is associated with the ascending reticular activating system (RAS) and its post-synaptic thalamic targets. The sources of P50 were subsequently and independently localized in the superior temporal gyrus using a MEG approach. Coregistered auditory evoked potentials (AEPs) and magnetic fields (AEFs) produced a resulting equivalent dipole model for the AEP consisting of one source in the auditory cortex of each hemisphere as well as a radially oriented medial frontal source.

Information regarding the visual P1 response differs from the auditory P1 literature in terms of the evoking stimulus, neurocognitive and neurophysiological mechanism, peak latency, scalp distribution, and neural sources. The visual P1 is typically recorded in a checkerboard-reversal task or similar light-flashes paradigms but can also be present for other visual stimuli (e.g., faces) and is largest over the occipital regions. A negative component may be present at the same latency over frontal and central regions. The amplitude of P1 generally varies with the amount of attention in Posner's attention cueing paradigm and in spatial selective attention experiments. It has been proposed that P1 reflects suppression of noise because the amplitude decreased for unattended locations and did not increase for attended stimuli. The P1 amplitude also increased when speed of response was emphasized, suggesting that P1 may also reflect the level of arousal.

Probable sources were identified using PET, BESA, and LORETA methods in ventral and lateral occipital regions, suggesting a striate or extrastriate (posterior fusiform gyrus) origin. A face identification paradigm reported similar sources as well as sources in posterior-parietal regions, suggesting the additional involvement of dorsal and ventral neural components.

The N1 component typically occurs approximately 100 ms after stimulus onset and is one of the most easily identified components regardless of the specific analysis approach employed. There is good convergence in findings based on analyses of PCA factor scores, baseline to peak amplitude, and baseline to peak latency.

Generally, N1 is assumed to reflect selective attention to basic stimulus characteristics, initial selection for later pattern recognition, and intentional discrimination processing. Latency and amplitude of the peak depend on the stimulus modality. Auditory stimuli elicit a larger N1 with shorter latency than visual stimuli.

For auditory stimuli, N1 has a maximum amplitude over frontocentral areas or the vertex. More recent studies differentiated it into three different components with maximum amplitudes over temporal areas (latency 75 ms and 130 ms) and over vertex (latency 100 ms). Based upon review of the three components of N1, it was proposed that the early temporal and vertex components reflect sensory and physical properties of the stimuli (e.g., intensity, location, timing in regards to other stimuli) while the later temporal component appears to be less specific in its response and reflects transient arousal. However, the majority of the studies reviewed in the present manuscript treated N1 as a single component occurring at 100 ms after stimulus onset with maximum amplitude at the vertex electrode.

The amplitude of the auditory N1 is enhanced by increased attention to stimuli and by increasing the inter-stimulus interval. The latter has been attributed to contributions of additional sources from frontal cortical areas. N1 appears most likely generated by sources in primary auditory cortex in the temporal lobe. MEG, BESA, and lesions studies consistently localize auditory N1 in superior temporal plane. However, several studies proposed additional sources in the frontal lobe that could be activated from the temporal lobe.

The visual N1 component is usually largest (maximum) over the occipital region or the inferior temporal regions. N1 amplitude is typically larger in discrimination tasks, but is reduced when stimuli are presented at short intervals. The N1 discrimination effect is attributed to enhanced processing of attended location and not due to arousal because the amplitudes were larger in a task that placed no emphasis on the speed of response. It is also not affected by inhibition as indicated by the lack of Go/No-Go response differences. Additionally, similar to the auditory N1, a visual N1 also occurred at 100 ms over the central midline sites and at 165 ms over the posterior sites. The researchers attributed the anterior N1 solely to response preparation processes because it could be eliminated by not requiring a motor response.

Using a combination of techniques (MEG, ERP, and MRI), the visual N1 sources were located in the inferior occipital lobe and the occipito-temporal junction. However, using the LORETA approach, additional sources of the visual N1 were identified in the inferior temporal lobe.

The P2, like the N1 and P1, has long been considered to be an "obligatory cortical potential" since it has low interindividual variability and high replicability. The P2 component has been identified in many different cognitive tasks including selective attention, stimulus change, feature detection processes, and short-term memory. P2 is sensitive to physical parameters of the stimuli, such as loudness. Participant differences, such as reading ability, can also change the P2 amplitude to auditory stimuli.

In the auditory modality, P2 often occurs together with N1, yet the two peaks can be dissociated. The distribution of the P2 is less localized than that of the N1 and has the highest amplitude over the central region. Also, the temporal peak of the P2 can occur over a broader latency range than the preceding peaks with latency ranging from 150-275 ms, and can be double-peaked. Similar to N1, P2 has been consistently identified by PCA factor scores, baseline to peak amplitude, and baseline to peak latency analysis procedures.

Generators for the auditory P2 are thought to be centered mainly in the primary and secondary auditory cortices. When using dipole source analysis, both the N1 and P2 elicited by auditory stimuli are often represented by two dipoles: one for the primary auditory cortex and one for the secondary auditory cortex. Using BESA and LORETA to identify dipole locations for the N1/P2 component, one in the superior temporal region was identified with a tangential orientation while the second was located in the temporal lobe with a radial orientation. These dipoles reflected the primary and secondary cortices respectively. However, it is difficult to differentiate the peak-specific locations because dipole source analysis is still relatively primitive, making it difficult to disentangle the individual effects of the neighboring structures.

In the visual domain, the amplitude of P2 increases with the complexity of the stimuli. Topographic distribution of the visually elicited P2 is characterized by a positive shift at the frontal sites around 150-200 ms after stimulus onset and a large negativity, approximately 200 ms following stimulus onset at the occipital sites. Using BESA dipole analysis, a symmetrical dipole pair localized in the inferior occipital (extrastriate) areas was reported. The findings suggested that both topographic distribution and dipole position varied slightly when attending vs. not attending to the visual images.

Very few studies have investigated the "basic" N2 peak; rather, it is considered to be a family of responses that differ based on features of the experiment, such as modality and stimuli presentation parameters. These components share some of their functional interpretation with mismatch negativity (MMN; see below) because both appear to indicate a detection of a deviation between a particular stimulus and the subject's expectation. However, unlike the MMN, in order for N2 to be present the subject must pay attention to the stimuli. In a study, participants viewed two stimuli; the first was expected to give information about the image that was to follow. When the following image did not match what was expected, they observed a larger N2 with frontal distribution, compared to when these expectations were met.

The N2 component has multiple psychological interpretations including orienting response, stimulus discrimination, and target selection, possibly reflecting task demands. Further, N2 is characterized by higher interindividual variation. Findings also show that the N2 is smaller in amplitude and shorter in latency for shorter interstimulus intervals.

The topographic distribution of the N2 depends on the sensory modality of the stimulus. Specifically, auditory stimuli elicit the highest N2 amplitudes at the vertex. Based on scalp current density analysis, it has been suggested that the N2 has bilateral sources in the supratemporal auditory cortex.

It has been reported the N2 amplitude reached its highest over the preoccipital region. While traces were reported of frontal activity, this frontal activity did not contribute appreciably to the visual N2 distribution. Further, N2 to visual stimuli varied based on the stimuli type, such as written words, pictures of objects, or human faces. Using intracranial electrodes placed directly on the cortex, it has been observed that letter-strings of recognizable nouns produced a N2 component at the fourth occipital gyrus near the occipitotemporal sulci. Pictures of complex objects, such as cars and butterflies, resulted in an N2 response over the inferior lingual gyrus medially and the middle occipital gyrus laterally. However, this effect was not present for the scrambled pictures. Face recognition tasks elicit an N2 over the fusiform gyrus and inferior temporal or occipital gyri just lateral to the occipito-temporal or inferior occipital sulci. The differential processing of human faces has led many researchers to investigate the visual processing of human faces (see N170 below). These differing distributions indicate that the N2 peak may reflect category-specific processing The N2 is also associated with the Go/No-Go paradigm, in which the participant is asked to respond to some stimuli (Go trials), but inhibit the response to another class of stimuli (No-Go trials). The ERPs on No-Go trials are characterized by a large negative peak relative to the Go trials between 100 and 300 ms after stimulus onset. Given the nature of this task, it is often thought to be associated with response inhibition; it has been shown, though, that this response occurred both in relation to overt and covert responses, indicating that the N2 Go/No-Go effect cannot be completely attributed to motor responses. Instead, it appears to be present whenever responses must be interrupted.

The amplitude and polarity of the N2 inhibition response can change depending on the complexity of the task. In some instances, the Go/No-Go response has been reported as a positive peak. It has been suggested this pattern was due to large amplitude of the P300 in difficult tasks. Similarly, the effect is larger when subjects have less time to respond.

The N2 for the visual and auditory task is especially strong over the fronto-central electrodes when the Go response is withheld. This scalp distribution is different from that of the Error Related Negativity (ERN) that occurs approximately 125 ms after an incorrect response is made. It has been shown that the N2 response engages different processes than the error monitoring processes reflected in the ERN.

Using both ERP and fMRI, the involvement of the caudal and motor anterior cingulate cortices has been identified during both correctly and incorrectly inhibited responses. These sources differed from ERN responses that were related to caudal and rostral anterior cingulate cortices, providing additional support to the theory that the N2 reflects inhibitory responses that are distinct from the error-related negativity.

The N170 peak ranges in peak latency between 156 and 189 ms and is associated with visual processing of human faces. The topographic distribution of the N170 component for both familiar and unfamiliar faces is largest over the occipito-temporal regions. Its amplitude is significantly larger when viewing faces than when viewing other natural or human-made objects. Additionally, patients suffering from prosopagnosia do not show an N170 response to faces. It has been argued that the N170 is not specific to human faces but to expert object recognition, finding that dog experts showed an increased N170 to pictures of dogs but not birds, while bird experts showed the opposite effect.

Intracranial recordings of evoked potentials and fMRI studies all point to the fusiform gyrus as the possible neuroanatomical substrate of N170. However, source localization of the N170 using BESA identified the potential source in lateral occipitotemporal region outside the fusiform gyrus.

The MMN wave is a negative deflection that has a typical latency of 100-250 ms. The amplitude is largest at frontal and central electrode sites. MMN is elicited using an "oddball paradigm" where an occasional deviant stimulus is presented in a stream of more frequent standard stimuli. Because MMN paradigms require no attention to the stimuli, they have been widely used in developmental research and sleep studies.

In the auditory modality, the MMN can be evoked by any perceivable physical deviance from the standard stimulus, such as changes in tone duration, frequency, intensity, and interstimulus interval. It is thought to be an index of the early, preattentive sensory memory, most likely only echoic memory. Most often MMN is used to test the ability of the subject to discriminate linguistic stimuli (e.g., speech sounds with different voice onset time or place of articulation. Frequently, data are analyzed by subtracting the average ERP elicited by the standard stimuli from the average ERPs for the deviants. This subtracted component generally displays an onset latency as short as 50 ms and a peak latency of 100-200 ms.

Using MEG, significant differences have been found between dipoles produced by deviants that differed in intensity, frequency and duration. Dipoles for frequency and duration deviants were located significantly inferior in comparison to the source of intensity deviants and differed significantly from each other in the anterior-posterior direction. All dipoles were located within the temporal lobes. fMRI and ERP data were recorded simultaneously to an MMN task. Increased BOLD signal were found were in the right superior temporal gyrus and the right superior temporal plane.

Though MMN is associated with considerable high test-retest reliability, it is important to note that many features can influence the outcome of the MMN. While most researchers report a negative wave in association with the MMN, there have been reports of a positive wave around 200 ms corresponding to the MMN response. The exact reason for this difference has not been thoroughly investigated but may be due to differences in filter settings. Also, some reports indicate a substantially reduced MMN response in subjects not attending to the stimuli. Similarly, the probability of the deviant stimuli can influence the nature of the effect. Given the use of ERP averaging to remove noise from the data, researchers must maintain a balance between presenting enough deviant trials to obtain low-noise average responses, and not allowing the subject to habituate to the deviant, thus diminishing the effect. The habituation of adults, children, and guinea pigs were mapped for complex and simple stimuli using the MMN paradigm. It was found that as the number of exposures increased the size of the MMN response decreased (though not in a linear fashion), but that time for habituation varied as a function of the complexity of the stimuli.

The MMN for visual stimuli has been difficult to obtain, although there is some evidence that it can be captured with optical techniques. Source localization techniques suggest the involvement of the primary visual cortex and/or adjacent areas.

At this time, the P3 is the most extensively researched ERP component. A pronounced positivity occurs in response to an unexpected stimulus type approximately 300 ms after stimulus onset. Currently, the most typical paradigm for eliciting the P3 component, also known as P3b, is the oddball paradigm where a target stimulus is presented infrequently among more common distracter stimuli. However, the P3 could also be elicited in a single stimulus paradigm where a rare stimulus is presented randomly in time. For a P3 to be elicited, the subject must pay attention and respond to the stimuli (unlike the MMN paradigms) and the ratio of target to distracter stimuli must be low (the fewer targets the larger the peak). P3 amplitude is affected by attention, stimulus probability, and stimulus relevance as well as by the amount of processing resources available, such as in single vs. dual tasks, the quality of selection, and attention allocation. The length of the interstimulus interval could also affect the amplitude independently of stimulus probability with shorter intervals resulting in a larger P3. P3 latency was reported to vary with stimulus complexity, effectiveness of selection and sustained attention.

The visual P3 is larger and has a longer latency than the auditory P3. In a 3-stimulus oddball paradigm, a larger P3 was reported for target vs. nontarget auditory stimuli, while visual stimuli elicited a larger P3 than auditory stimuli. P3 was largest over parietal regions and midline. Auditory stimuli elicited shorter latency P3 over parietal regions and longer latency over central sites.

The functional interpretation of the classic P3 is diverse—some view it as an indicator of memory updating while others believe that it reflects a combination of processes that vary by task and situation, including more elaborate active stimulus discrimination and responses preparation. P3 latency is assumed to reflect the duration of stimulus evaluation. The P3 component has also attracted attention in clinical studies. Because P3 amplitude varies with the amount of attention paid to the stimuli, this component is widely studied in populations with attention deficits (e.g., ADHD) where it is interpreted to reflect information regarding various attentional functions. Further, P3 latency was reported to be related to cognitive abilities with shorter latencies associated with better performance.

Sources of the P3 are not clearly identified but at least some are expected to be in the medial temporal lobe, including the hippocampal region related to memory, parahippocampal gyrus, amygdala, or thalamus. Lesion data suggest that there may be multiple generators, including the temporo-parietal junction. The possible sources were investigated and reported that selecting only one region (e.g., hippocampus or thalamus) resulted in poor model fit, but combining the different locations produced a better model. Their findings are consistent with earlier observations using MEG analyses that located sources in the floor of Sylvian fissure (superior temporal gyrus) as well as deeper sources in the thalamus and/or hippocampus.

A variant of P3, known as P3a, appears to have a different scalp distribution with frontal maximum and slightly shorter latency for stimuli in visual vs. auditory, and somatosensory modalities. This frontal P3a occurs when a subject is not required to actively respond to the targets or when a novel stimulus is added to the standard 2-stimulus oddball paradigm.

Frontal P3a is assumed to reflect involuntary attention as well as inhibition. In Go/No-Go paradigms, P3a was larger in amplitude in No-Go than Go conditions (maximal at parietal sites for Go). Regarding its neural substrate, sources of P3a have been identified in the medial parietal lobe (early: 317 ms) and in the left superior prefrontal cortex (late: 651 ms) for Go trials; for the No-Go trials (365 ms) the sources originated in the left lateral orbitofrontal cortex. Underscoring the prefrontal cortex connection, P3a can be reduced by lesions to frontal cortex.

The N400 negative component occurs approximately 400 ms after stimulus onset and is usually associated with semantic comprehension in both visual and auditory sentence comprehension tasks. This phenomenon was first identified in a paradigm where words of a sentence were visually presented one after another at fixed intervals in a serial manner. The last word of the sentence was either congruous ("He took a sip from the water fountain") or incongruous but syntactically appropriate ("He took a sip from the transmitter") with the rest of the sentence. The incongruous words elicited a larger amplitude N400 response than the congruous words. Further, the amplitude of the N400 was correlated with the degree of incongruency of the sentence to the final word. It was found that the N400 effect only held true for semantic, but not syntactic deviations from expected endings. Evidence indicates that listeners use the information gained from the wider discourse when interpreting the appropriateness of a particular word. The N400 is also elicited in semantic word pairs, semantic priming tasks and matching semantic material to visual displays.

In both visual and auditory displays, the N400 is larger for anomalous endings than expected endings over the parietal and temporal regions of the right hemisphere. There are differences in the N400 based on the modality of the task. The peak of the N400 is earlier in the visual (475 ms.) than auditory (525 ms) modality but only over the temporal, anterior temporal and frontal sites. Further, the earliest peak in the visual modality was over the parietal and temporal sites, while in the auditory modality it was over parietal and occipital sites. Asymmetries (with activation in the left hemisphere occurring earlier than activation in the right) were only noted in the visual modality. The N400 does not appear to be specific to written words, because spoken words and pictures can elicit this response. The N400 response was also elicited by incongruent solutions to mathematical multiplication problems.

The amount of attention necessary to produce the N400 and the precise cognitive processes involved remain unclear. It has been reported that the N400 is more robust with when attention is required but can occur even when participants are not attending to the stimuli. However, it has been reported that in a dichotic listening task, the N400 was absent for material presented in the unattended ear. The amount of effortful semantic processing required is also unclear. It has been reported an N400 effect even in tasks that did not require semantic processing although it has been found no N400 when the attention was not directed to the meaning of the stimuli. One consistent finding is that N400 can be elicited by anomalies in language presented in various modalities, including auditory presentation. However, N400 did not occur when participants were presented with anomalies in music, which is believed to involve a structure similar to language.

The N400 is likely to arise from multiple generators that are functionally and spatially segregated. Recent work points to the parahippocampal anterior fusiform gyrus as the generator for this effect. MEG studies have pinpointed the lateral temporal region as the origin of the N400 response. Intracortical depth recordings using written words point to the medial temporal structures near the hippocampus and amygdala.

The P600 component has two distinct functional interpretations, one associated with memory processes and another associated with language. Although the two variants of the P600 have roughly similar topographies, they appear to have different brain sources.

It has been suggested that the P600 component, especially the variant associated with language processes, is a delayed variant of the P3 because these peaks have relatively similar scalp distributions and are both sensitive to probability manipulations. In opposition to this view, it has been reported evidence that the P3 and P600 have sufficiently different scalp topography, are differentially sensitive to manipulations of stimuli and task, and have additive effects when they are co-elicited.

The P600 positive deflection typically begins at 400 ms, continues for approximately 400-600 ms, and is maximal over left temporo-parietal regions. This P600 old/new effect often co-occurs in time with a frontal N400 effect present over left fronto-central areas starting at 300-500 ms post-stimulus and continuing to 1200 ms and beyond. It has been noted that during the learning phase of a free recall task larger N400 and P600 amplitudes were elicited by items that were later forgotten. However, the two components have different functional interpretations. P600 is assumed to reflect recognition for the stimuli while frontal N400 is associated with stimulus familiarity.

Numerous studies of recognition memory reported a larger P600 in response to 'old' stimuli (previously presented to the subject) compared to 'new' stimuli that were not experienced before while the opposite is true for frontal N400. The P600 old/new effect also occurs for items that are incorrectly judged as 'new'. In addition, it is often larger for correctly recognized words than falsely recognized lures and can be affected by depth of processing, and the amount of retrieved episodic information. Further, the amplitude of the P600 peak increases with better memory performance. A number of experiments have demonstrated that P600 old/ new effects could also occur in the absence of intentional retrieval. However, some have reported that intentional retrieval resulted in enhanced P600 old/new effects.

Although most of the P600 studies involve visually presented stimuli, some work has employed auditory stimuli. For example, it has been noted no difference in the size of the P600 when the words were studied in one modality but tested in another. Similarly, it has been reported the old/new P600 effect after training subjects on auditory stimuli and testing them when the same stimuli were presented visually. These findings suggest that the component is not modality specific.

Various techniques consistently identified several brain sources for the P600 old/new effect. Using intracranial ERP recordings during continuous recognition tasks, it has been noted that P600 responses in prefrontal regions and anterior temporal lobe structures. Further, it has been reported that a large amplitude P600 response in the anterior cingulate gyrus. Similar findings were obtained in studies employing PET and ERP methods. PET data indicated that rCBF in the left posterior hippocampus, left frontal and temporal cortex, and left anterior cingulate were greater during the recognition of deeply processed (sentence generation vs. alphabetic judgment) words. Event-related fMRI imaging has been utilized and found that during the study period, words subsequently given recalled versus familiar judgments were associated with increased activity in a posterior left prefrontal region. However, during the memory task, recalled words were associated with enhanced responses in anterior left prefrontal, left parietal, and posterior cingulate regions relative to familiar judgments.

It has been reported that syntactic anomalies elicited a small early negativity and a small later positivity rather than a N400 response. A decade later, two independent research teams identified a specific component, variously referred to as P600 or the Syntactic Positive Shift. This component consists of a slow positive shift, lasting up to 300 ms, that begins approximately 500 ms after word onset and is widely distributed across the scalp, with a posterior maxima.

The syntactic P600 is typically elicited by various syntactic or morphosyntactic violations, including violations of agreement, phrase structure, subcategorization frame, and subjacency. It has also been elicited by syntactically ambiguous sentences. This syntactic P600 was reported in studies using various languages, such as English, German, and Italian. Syntactic P600 is also thought to reflect additional grammatical processing performed in response to a parsing failure (Hagoort, et al., 1993; Osterhout, 1994; Friederici & Mecklinger, 1996). Although the P600 is usually elicited by means of visually presented written stimuli, it can also be elicited using naturally produced speech (Friederici, et al., 1993; Hagoort & Brown, 2000).

Investigation of the neuroanatomical sources of the syntactic P600 using rapid-presentation event-related fMRI methods identified greater activation in the superior parietal cortex and the precuneus and posterior cingulate on the medial surface in response to morphosyntactic violations compared to normal sentences (Kuperberg, et al., 2003). An ERP study of 14 aphasic patients with lesions in basal ganglia or in temporal-parietal areas noted that only the group with basal ganglia lesions failed to display a P600 effect in response auditory stimuli containing syntactic violations (Frisch, et al. 2003). However, both groups displayed a clear P300 effect for the P3b in response to an oddball paradigm. Such results suggest that the basal ganglia play a crucial role in the modulation of the syntactic P600.

From the review, it is evident that a notion of specific peaks reflecting specific cognitive processes is a long outmoded view. In the early years of electrophysiological research, equipment limitations made it very difficult or impossible to record and/or analyze more than a single peak or to record from more than a few electrode sites. This may have led investigators to conclude that the measured component was the sole indicator of the cognitive process in question. In the interim, decades of research and advances in technology have increasingly demonstrated that each of the ERP components can be elicited by multiple stimuli and paradigms that tap different cognitive processes. This view is in line with the common understanding of brain organization—the same structures may participate in different processes to varying degrees at different times.

Further, it clear that peak characteristics can be affected by the procedures used to record ERPs. Differences in number of trials or length of intertrial intervals, variations in stimulus intensity or modality can contribute to inconsistent outcomes. Therefore, to increase the chance of successful replication, investigators must routinely report (and review) such details.

There are potential problems of interpretation, directly linking the scalp distribution of an ERP component with brain structures located below the specific electrodes. Brain sources of the components are often located not immediately below the electrode that recorded the maximum amplitude. In some cases, the sources are not even in the same hemisphere. Development of carbon electrodes as well as brain source analysis software now allows researchers to co-register EPRs with fMRI methods to map ERP components onto brain structures and to model potential sources of the observed activity across procedures.

Most scientific studies to-date have used discrete statistical methods to evaluate the ability of specific ERP tests to discriminate various neurological attributes between test subjects. This involves identifying the relevant peaks and comparing the amplitudes and latencies between different test subjects. Statistical distributions are calculated and cluster analyses are performed to ascertain if the peak amplitude and latency values correlate in some way with various neurological attributes, abilities, and/or disabilities. Discriminate analyses as described above have used ERPs to evaluate IQ, reading ability, language skills, Alzheimer's, attention deficit hyperactivity disorder (ADHD), and many other cognitive factors.

The tremendous clinical potential of the ERP method has been well recognized although because of certain system and methodological limitations this potential has only rarely been realized. These problems generally fall into four areas: (1) complicated, difficult to use, and incompatible hardware systems; (2) lack of standardized testing protocols including: stimuli, stimuli sequencing and timing, signal processing, testing environment; (3) analytical methods which do not provide statistically powerful or reproducible results, due to signal processing limitations, non-algorithmic peak detection methods, and disregard for information in the ERPs other than the peaks, and (4) requirement to perform large population studies in order to discriminate small neurological variations.

In addition to these shortcoming, and others noted in the research, it would be desirable that a system for performing ERP tests and analyzing the resulting data be developed that would be suitable for the clinical environment. The equipment expense, level of training required to perform these brainwaves studies, and unreliable results renders them impractical for widespread screening and diagnostic use.

Consequently, a significant need exists for an ERP testing system and method that is suitable for widespread clinical use.

BRIEF SUMMARY OF THE INVENTION

The invention overcomes the above-noted and other deficiencies of the prior art by providing an auditory and/or visual ERP testing system which is easy to configure and use; enables standardized protocols and methods; facilitates testing of a broad range of neurological attributes and disorders; and delivers reliable and reproducible results. This system employs an integrated, software controlled headset which presents the stimuli and records the ERPs. The headset is programmed through a web-enabled software control panel. The testing protocols and stimuli are downloaded from an online protocol database. The resultant test data is uploaded from the headset to an online database. Various neurological attributes are classified using an automatic analysis method. And finally, results are available for display via a web-enabled software application. Such analyses are facilitated by associating testing paradigms and patient identification information with test results. Thereby, multiple types of ERP analyses by be performed for a range of neurological conditions.

In one aspect of the invention, an ERP system includes a configuration that is a set of parameters that control administration of a single test. These parameters include: when the stimuli should be presents; what stimuli should be used; the sequence of the stimuli, test error and failure parameters; and how data should be captured. Each configuration may be used to screen for a different neuropathology; ie, a configuration which performs a brainstem evoked response (BSER) test for hearing deficits, or a configuration which performs a mismatched negativity (MMN) test for dyslexia screening.

In an additional aspect of the invention, an ERP system has a distributed network architecture that meets the needs for economical testing a clinical locations, yet provides advantages of a standardized large population test data repository at a remote site. Test protocols may be user-defined and then stored on a remote and/or distributed element, such as accessed over the Internet or similar network, for later use. Similarly, test protocol configurations, stimulus files, and results may be stored in a remote and/or distributed database. This may include having all protocols used in any test which results in data being captured to be permanently stored in a centralized database for data integrity, economic processing, and large population analyses and research validation. Typically, all results stored in the centralized database may be related to a particular test protocol, allowing results to be queried by test protocol parameters. All stimulus files used in any testing protocol that results in data being captured may be permanently stored in a centralized database.

In another aspect of the invention, a sound synthesizer generate stimulus files based upon configurations that may include frequency, duration, sequence, and time warp. With regard to the latter, a time warp sound stimuli may be a stimulus with lengthened duration with an unchanged tone.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 10 is a table of a stimulus library maintained and utilized by the ERP screening system and/or the ERP headset of FIG. 7.

FIG. 11 is a table of a stimulus sequence library maintained and utilized by the ERP screening system and/or ERP headset of FIG. 7.

FIG. 12 is a table of data capture settings maintained and utilized by the ERP screening system and/or ERP headset of FIG. 7.

FIG. 14 is a diagram illustrative of the stimulus sequencing logic of various ERP paradigms.

FIG. 17 is a depiction of a graphical user interface (GUI) for login to a control panel of the ERP screening system of FIG. 7.

FIG. 18 is a depiction of a GUI for system registration of an ERP headset of the ERP screening system of FIG. 7.

Figure 21:
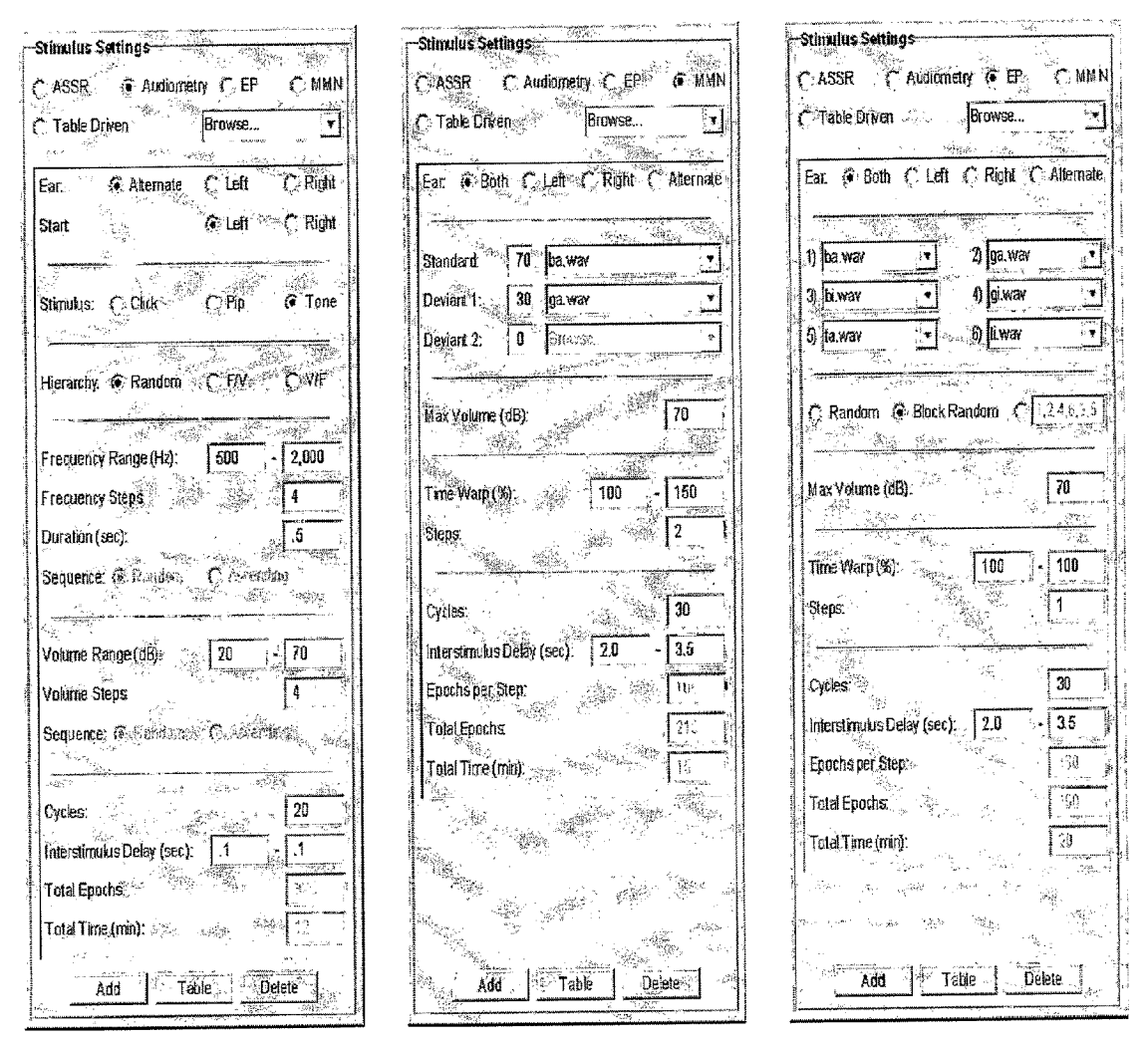

FIG. 21 is a depiction of a GUI for stimulus sequences and settings for an ERP headset of the ERP screening system of FIG. 7.

Figure 22:
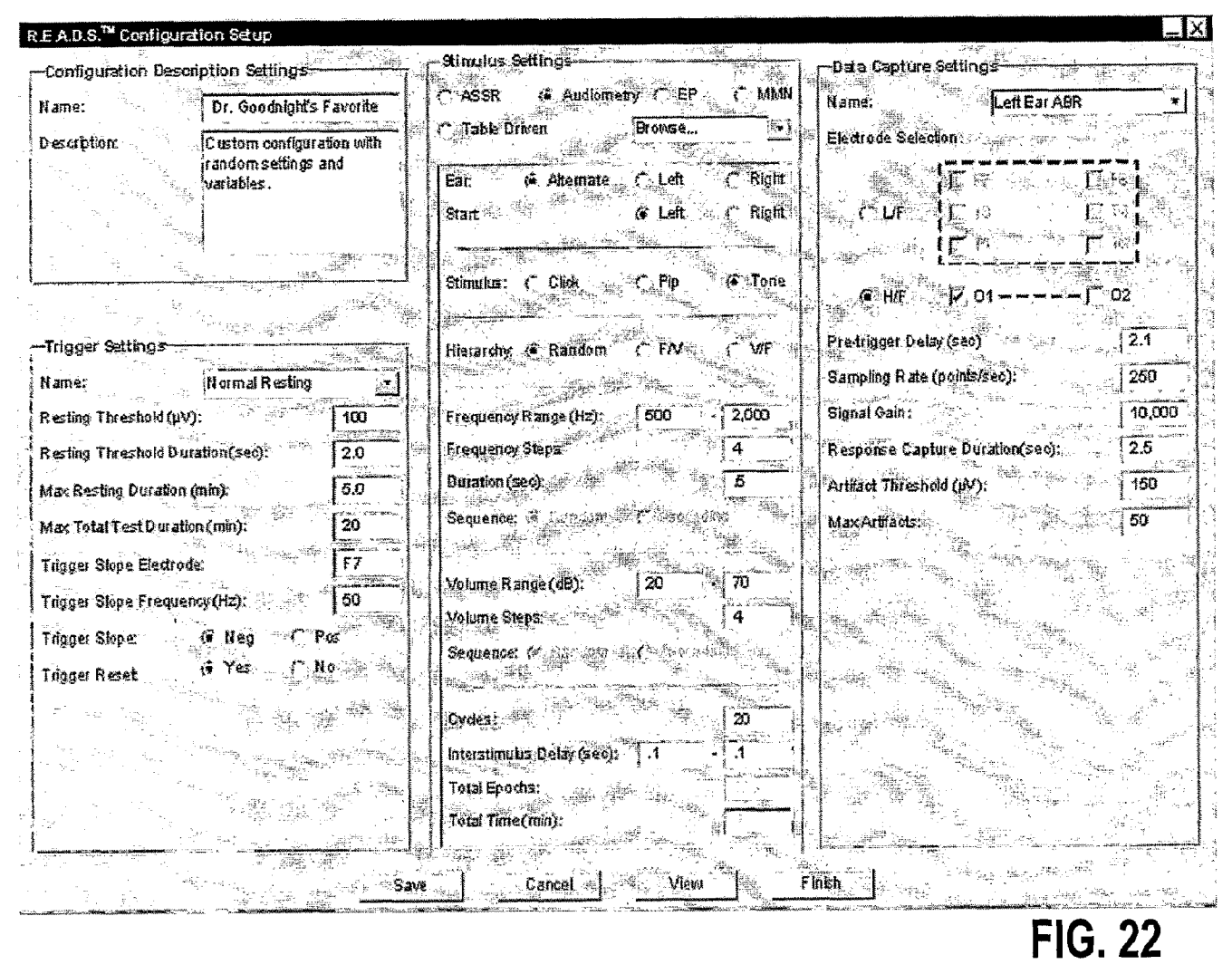

FIG. 22 is a depiction of a GUI for configuration setup for an ERP headset of the ERP screening system of FIG. 7.

FIG. 23 is a depiction of a GUI for screening data upload for an ERP headset of the ERP screening system of FIG. 7.

DETAILED DESCRIPTION OF THE INVENTION

Figure 1:
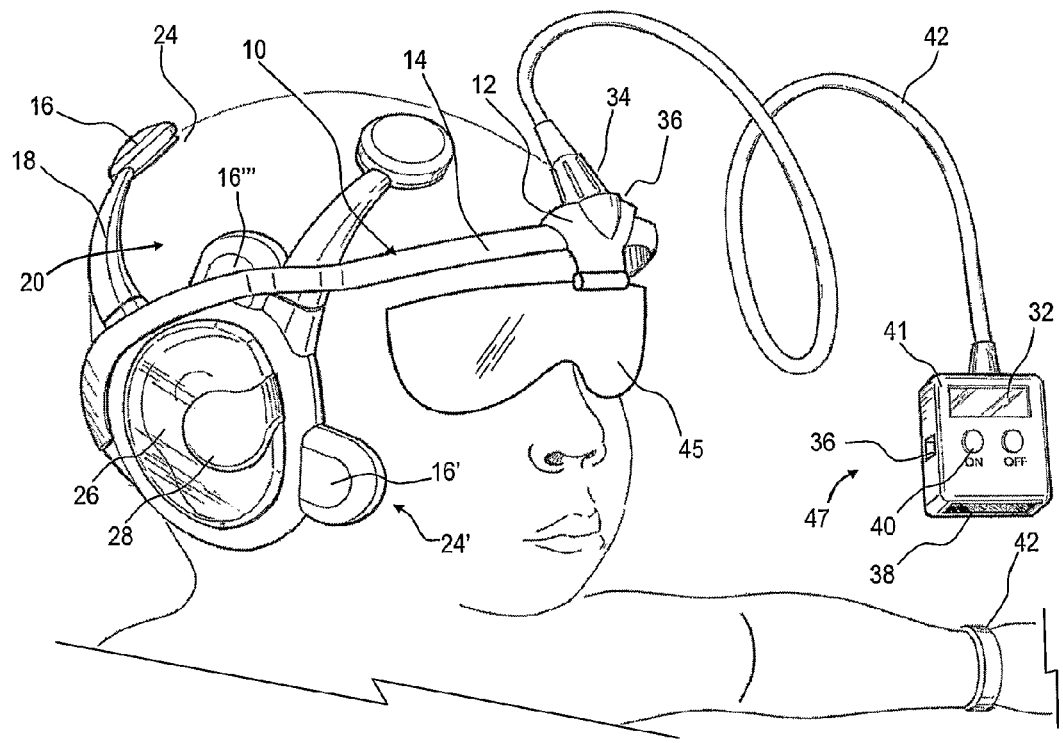
FIG. 1 is a perspective view of an integrated Auditory/Visual Evoked Response Potential (ERP) headset for clinical screening of neurological disorders (e.g., dyslexia, autism, etc.).

In the drawings where like members are given the same reference numeral, in

FIG. 1, an integrated Evoked Response Potential (ERP) headset 10 includes embedded features that enable clinicians to readily perform an ERP test without the necessity of extensive training. Portability of diagnostic data taking allows use whenever and wherever desired. Economy of use is achieved by centralized processing of the diagnostic data so that a great number of headsets 10 may be used without the necessity of expensive waveform processing equipment at each location. Collecting data from many screened individuals enables enhanced and improved diagnostic algorithms to be created and implemented. Furthermore, the headset 10 includes features that speed its use while avoiding human error and the need for extensive training.

To these ends, the ERP headset 10 incorporates a control module 12 that advantageously allows the headset 10 to be portable and to be used in a clinical setting by including pre-loaded or downloadable testing protocols managed by the control module 12, enhancing ease of use. The headset 10 further includes an elastic, semi-rigid frame 14, which contains the control module 12. In particular, the frame 14 automatically positions six conductive electrode plugs ("electrodes") 16 via flexible arms 18 to specific positions relative to the ears of the testing subject 20 correlating to portions of the brain responsible for auditory or visual processing. These flexible arms 18 are advantageously cantilevered to exert a force upon the electrodes 16 to assist in obtaining good electrical contact with the subject's skin. In the illustrative embodiment, this alignment is assisted by the recurved frame 14 oriented to pass over the forehead. Alternatively, the frame 14 may be reversed so that the control module 12 is oriented behind the head 20. This convenient positioning greatly simplifies the generally accepted practice of manually positioning each electrode on the scalp in reference to a central point. One or more similar reference electrode plugs 16' are positioned by the headset 10 locations of the subject selected for being relatively at an electrical ground potential relative to the auditory processing locations and for being readily accessible with a supine subject.

Each electrode plug 16, 16' contacts the subject's skin via an electrode pad 24, 24' that includes electrical contacts to pick up the voltage signal of the ERP. The frame 14 and flexible arms 18 exert a force respectively upon each electrode plug 16, 16' and electrode pad 24, 24' to achieve a good electrical contact. Each electrode pad 24, 24' may be individually replaceable to ensure proper operation and/or sterilization requirements. Alternatively, a larger portion of the headset 10 may be replaceable for such reasons. Yet a further alternative may be that the electrodes 24, 24' may be compatible with sterilizing agents, such as an alcohol wipe. The electrode pads 24, 24' may support or incorporate an electrically conductive substance such as saline to enhance electrical contact. Alternatively or in addition, the electrode plugs 16, 16' and electrode pads 24, 24' may incorporate a pneumatic seal when manually depressed against the subject's skin, or even further include an active pneumatic suction capability to achieve good contact.

An exemplary electrode 24, 24' may employ an active digital electrode approach for incorporation into the headset 10 to address the need for sensitivity, enhanced signal to noise performance, and economy, described in greater detail in the afore-mentioned PCT patent application WO 05/010515.

Figure 3:
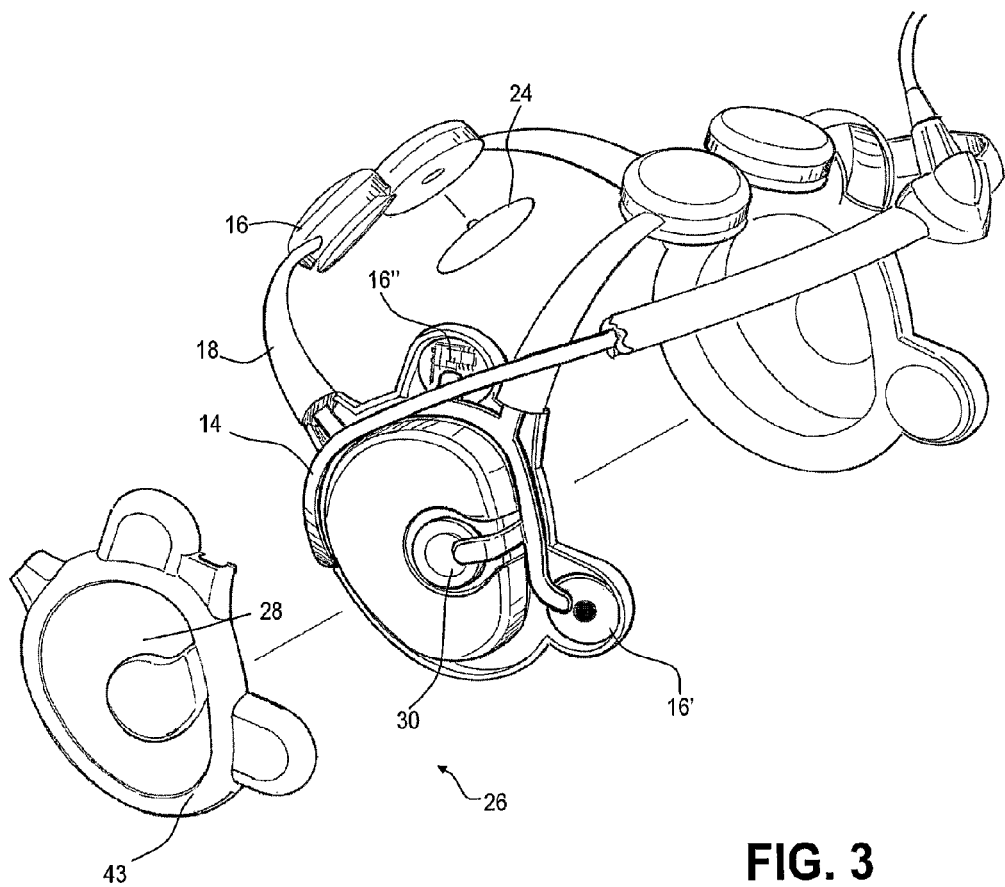
FIG. 3 is a perspective view of the ERP headset of FIG. 1 with one clamshell cover removed and the visor not shown.

In FIGS. 1 and 3, the frame 14 also supports ear cups (earpieces) 26 that position sound projectors 28 in front of the respective subject's ear. The headset 10 includes a speaker 30 (FIG. 3) for each ear that generates an auditory signal in response to an electrical signal from the control module 12. Each speaker 30 may be in a respective ear cup 26. Alternatively, each speaker 30 may be proximate to the control module 12, such as a piezoelectric transducer, that generates a sound that is directed through a pneumatic sound tube (not shown) to the sound projector 28 in the ear cup 26. This latter configuration may have advantages for having a replaceable ear cup assembly wherein active components are relegated to a reusable portion or where the active components are externally coupled to a passive, perhaps disposable headset. An electrode (not shown) may advantageously be included in the ear cup 26 for ensuring location caudad to the sylvan fissure.

Fluid-filled bladders (not shown) may be advantageously incorporated into portions of the headset 10, such as inside the ear cups 26 and electrodes 16, in order to provide a uniform contact with the subject's head, reducing discomfort and the likelihood of impedance variations. Alternatively, a resilient material (e.g., foam, gel) may be used instead of fluid-filled bladders.

In FIG. 1, a visual display device 45 may be advantageously incorporated into the headset 10 for the purpose of presenting a visual stimulus to the subject. The visual display device 45 may incorporate discrete illumination devices such as those used in PHOTOSONIX HEMISIM light stimulation glasses. Alternatively, the visual display device 45 may use video displays like those used in video glasses such as the INNOVATEK V190 or a head mounted display such as the DISPLAY SYSTEMS I-SCAPE IIIO.

When the headset 10 is used, simplified indications and controls 32 let the clinician know that the headset 10 is operational. For instance, an indication may be given that sufficient battery power exists and that the electronic components have passed a built-in test, etc. Thereby, the clinician, even with little specific training into the ERP waveform analysis, is able to readily perform the data acquisition on the subject.

Although the headset 10 may include all of the functionality required to perform a (e.g., dyslexia) ERP testing protocol, the headset 10 advantageously accepts an external electrical connector 34 at an interface 36 so that additional functionality may be selectively used. For instance, rechargeable batteries (not depicted in FIG. 1) in the headset 10 may be charged. The interface 36 may accept subject identification information to be linked with the diagnostic data taken. For instance, a personal computer, personal digital assistant, or a keypad 47 may be interfaced to the headset 10 as a means to input subject identification information. An illustrative input device, depicted as an identity scanning device 38, such as the OPTICON PN MSH-LVE4100 barcode scanner module integrated into a control box 41, is activated by a key pad, depicted as a push button 40, presented upon the control box 41 to read a patient identification band 42. The illustrative identity scanning device 38 advantageously has a short reach via cable connection 43 to minimize the likelihood of misidentifying the subject being tested. The identity scanning device 38 may advantageously sense alternatively or in addition to barcodes other indicia of identity, such as by passive radio frequency identification (RFID) (e.g., PHILIPS PN HTRM440), fingerprint scanning, or manual keypad entry via an input device coupled or attached to a control box. Furthermore, such control box functions may be integrated into the headset rather than being tethered thereto.

The keypad 47 may also be used as an input device used by the testing subject 20 when specific testing protocols require an active response from the testing subject 20. Certain paradigms require the subject to actively respond to a particular stimuli, audio or visual. ie; "press the button each time you see an animal". Stimuli: cat—dog—rabbit—cow—flower. This is called a "stop-signal" paradigm and evaluates the inhibition response (among others).

It should be appreciated by those skilled in the art having the benefit of the present disclosure that a hard-wired interface 36, such as a Universal Serial Bus (USB) interface, may be used as depicted or a wireless connection may be made, such as using the BLUETOOTH standard or other type of link.

Furthermore, a barcode identifier may be a one-dimensional or a two-dimensional barcode. Similar, the identifying information may be in the form of an embedded radio frequency (RF) target that puts off a unique return when energized by an RF carrier signal. Other types of identifying information may be used consistent with aspects of the present invention.

Figure 2:
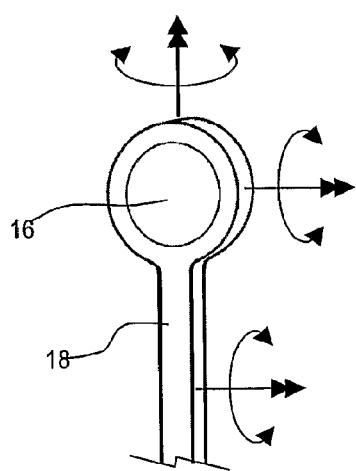
FIG. 2 is a close-up view of an electrode attached to one of the headset's flexible arms.

FIG. 2 depicts the flexible arm 18' supporting the electrode plug 16 annotated to denote resilient characteristics inherent so that a good electrical conduct is achieved. It will be appreciated that wiring or conductive ink applied to or formed therein may be used to electrically couple the electrode plug 16 to the control module 12.

Alternatively, it should be appreciated that reference electrodes may be supported upon flexible arms (not shown).

In FIG. 3, one or more active electrodes 16 may be a high frequency electrode which has been set to capture brainwaves at around 20,000 Hz. Disposable electrode contact pad 24, shown detached, may be impregnated with an electrolytic gel to lower impedance. This headset 10 includes three different types of electrodes. High frequency electrodes 16, reference electrodes 16' at the patient's cheek, and low frequency electrodes 16". As mentioned before, some electrodes 16 advantageously achieve good electrical contact via cantilevered flexible arms 18 while those closely coupled to the ear cups 26 receive a similar inward force from the recurved frame 14. Reference electrodes 1', along with the speaker 30, are captured in a clamshell cover 43.

Figure 4:
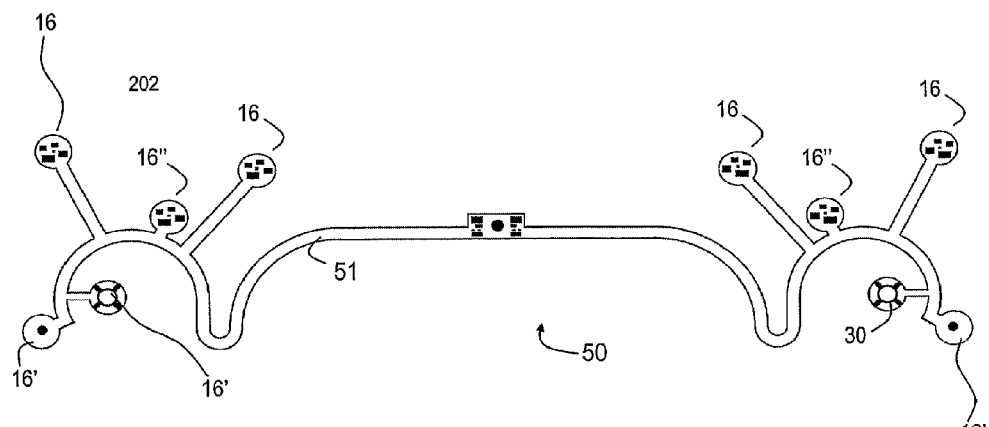
FIG. 4 is a top view of a flex-circuit electronic harness for the ERP headset of FIG. 1.

In FIG. 4, a flex-circuit electronic harness 50 is depicted as an economical fabrication approach with the electrodes 16, 16', 16" erconnects, and other headset electronics integrated onto a flexible printed circuit 52. Electrode electronics 54, control electronics 56, earpiece electronics 58, and electrode pad connectors 60 are electrically connected to flexible printed circuit 52. Thus, an advantageous flex-circuit electronic harness 50 lends itself to being shaped to a subject's cranium and to being exteriorly cantilevered into good electrical contact with the subject's skin.

Figure 5:
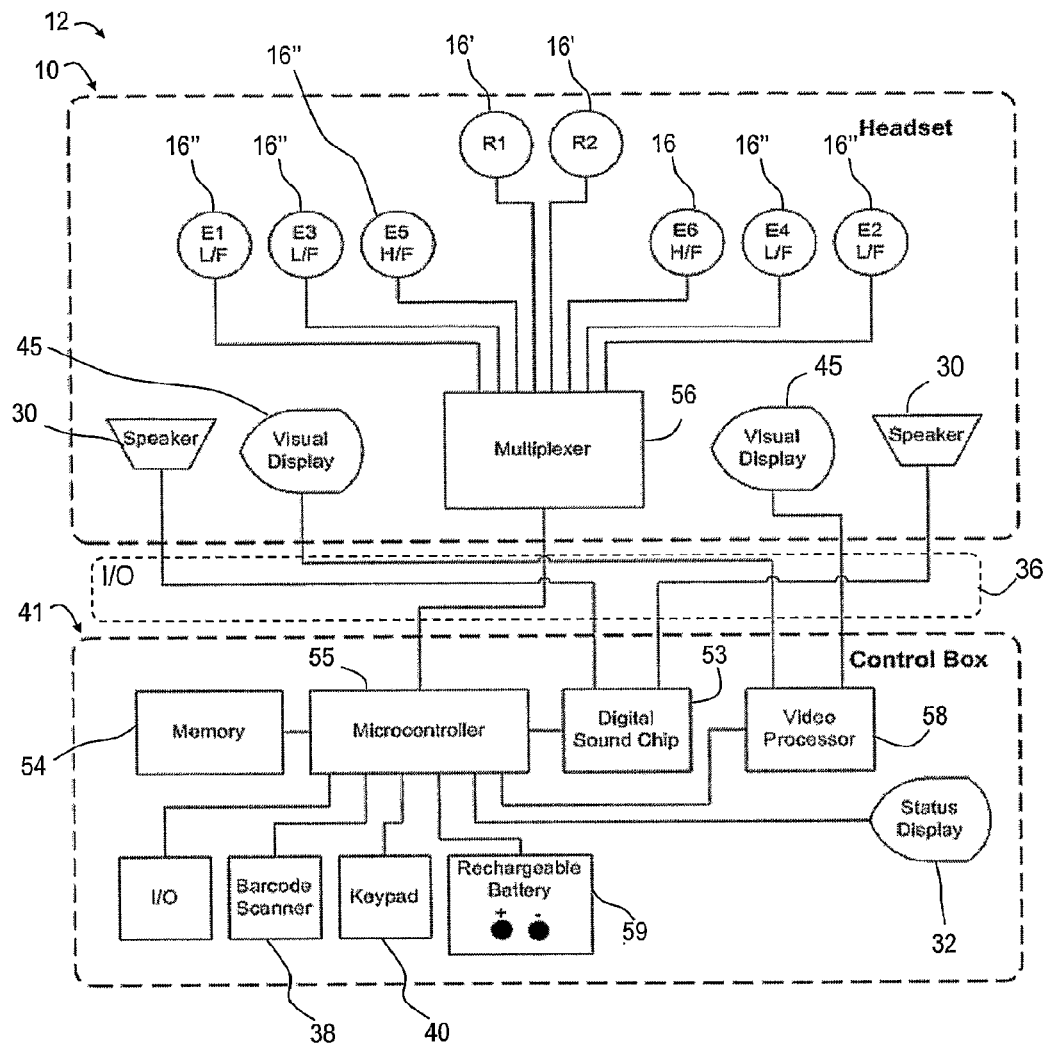
FIG. 5 is a functional block diagram of a controller of the ERP headset of FIG. 1.

FIG. 5 depicts an illustrative control module 12 of the headset 10 formed as an electronic circuit 53. It should be appreciated that the electronic circuit 53 may advantageously be produced in large-scale production as a custom Application Specific Integrated Circuit (ASIC) wherein all or many of these and other functions are incorporated into a single silicon wafer.

In the illustrative version, a number of discrete devices are used to perform the acquisition of ERP data. The electrodes 16, 16', 16" produce a low voltage signal that is selectively transmitted to the control box 41 by a multiplexer 72. At least one electrode 16 may advantageously be designed for high frequency data capture (e.g., typical sampling rate of 20,000 Hz) and/or at least one electrode 16" may be designed for low frequency data capture (e.g., typical sampling rate of 250 Hz). The gain, filters, and A/D conversion settings may thus be different to accommodate the differences in signal characteristics. In particular, the high frequency electrode(s) 16 may be used to capture low amplitude, high frequency brainwaves as in auditory brainstem response (ABR) testing for hearing defects. The low frequency electrode(s) 16" may be used to capture higher amplitude, lower frequency brainwaves like the middle latency response (MLR) and the late latency response (LLR). These waves are commonly used to detect auditory processing disorders (APD), attention deficit disorder (ADD), and dyslexia.

The multiplexed signal therefrom is received by an integrated memory 54, such as a TOSHIBA, Part. No. TC58128AFT, 128 MB 3.3V Flash Memory in a 48 Thin Small-Outline Package (TSOP) Surface-Mount Technology (SMT) package. The memory 54 within the control box 41 receives input data from external devices, such as the barcode scanner 38 via the interface (e.g., USB port) 36. The memory 54 is also preloaded or uploaded with a testing protocol and stores a number of testing session data records so that the headset 10 may be repeatedly used prior to uploading results.

The processing is performed by a microcontroller 55, such as MICROCHIP PIC16C765-I/PT, which advantageously includes analog-to-digital (A/D) Converters and USB Communication capability. An example of the processing includes sending a predetermined number of audio signals of a predetermined pitch, volume and duration or a previously recorded and digitized sound, and recording the resultant ERP waveform. Alternatively, visual signals may be used instead of or in combination with the auditory signals. In particular, the microcontroller 55 may communicate with the multiplexer 56 to control which electrodes 16, 16', 16" are being sampled. The electrodes 16, 16" can be turned on and off in a serial fashion to capture early, high frequency waves and later, low frequency waves evoked from the same initial stimulus. This will produce optimized signal detection with a minimum of file size.

The desired audio signals are produced by a digital sound card 57, such as by WINBOND ELECTRONICS, ISD4002-150E, "Single-Chip Voice Playback Device" that produces the audio signals on speakers 30. The desired video signals are produced by a video processor chip 58, such as the INTEL 2700G MULTIMEDIA ACCELERATOR that produces the visual stimuli on the video display 45.

The electronic circuit 53 is powered by a power supply 59, such as an ULTRALIFE UBC502030, Rechargeable 200 mAh battery.

Figure 6A:
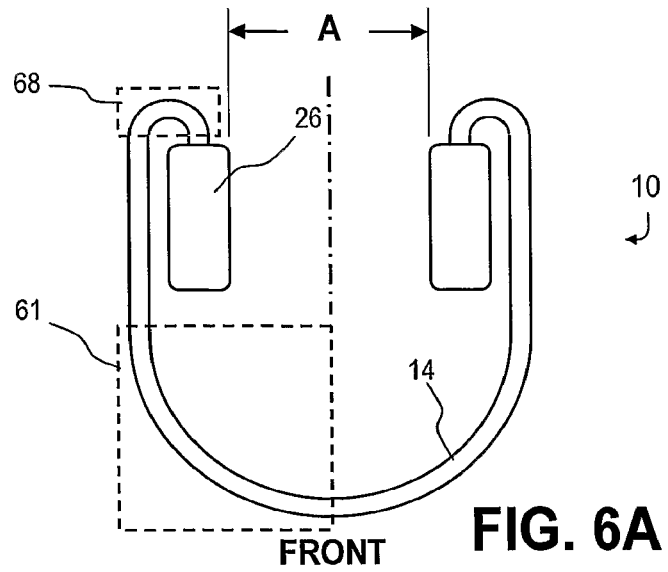
FIG. 6A is a top diagrammatic view of a recurved frame and earpieces of the ERP headset of FIG. 1, shown in a relaxed position.
Figure 6B:
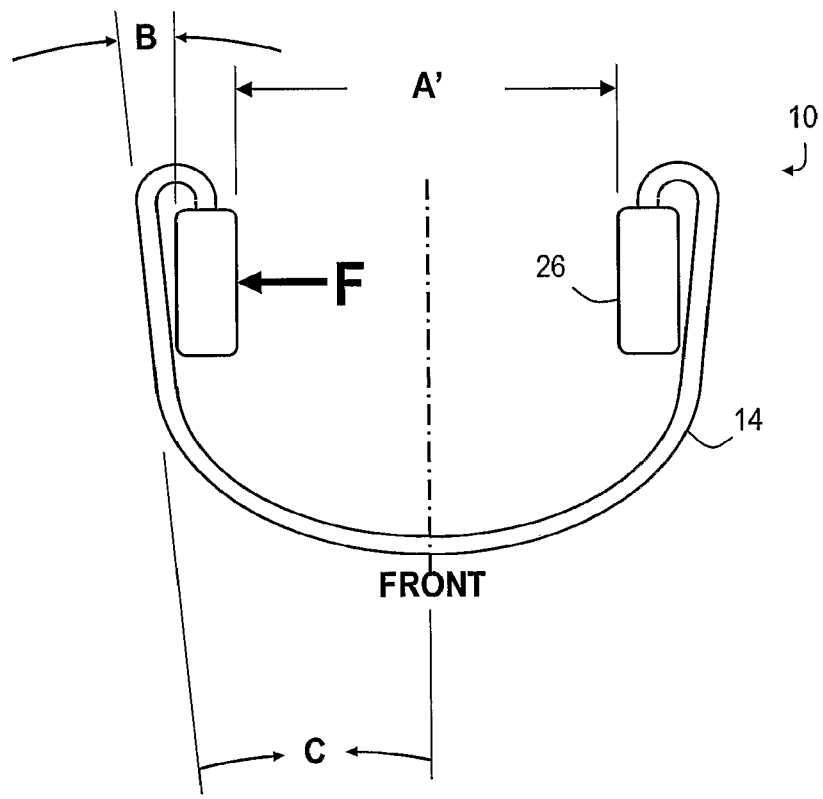
FIG. 6B is a top diagrammatic view of the recurved frame and earpieces of the ERP headset of FIG. 6A, shown in an expanded position.

In FIGS. 6A-6B, headset frame 14 is recurved such that when a force F is applied, as when there is a need for the headset 10 to be installed on a large head increasing the distance from A to A', the bending angle B of the ear cup 26 in the general area 60 aft of the ear cup 26 of the headset frame 14 is equal to the bending angle C of the headset frame 14 in the general area 61 forward of the ear cup 26. This will keep the orientation of the left and right earpieces 26, with respect to the subject's ears, the same for a broad range of head sizes.

Figure 7:
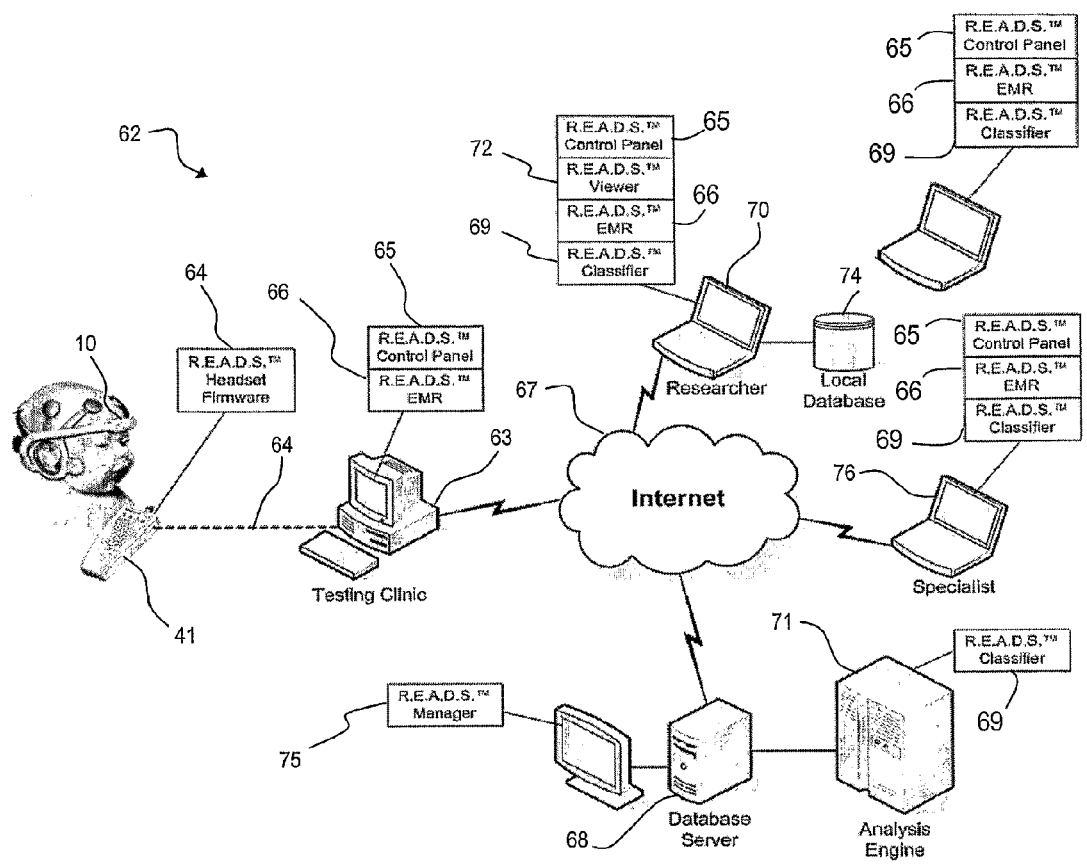
FIG. 7 is a block diagram of an ERP screening system and network connectivity.

FIG. 7 depicts an ERP (e.g., dyslexia) screening system 62 that advantageously provides for economical testing, billing, long-term data storage and analysis for analysis refinement, subsequent therapeutic measures, and other features. To this end, the headset 10 and control box 41 may be in electrical communication with a hospital system 63 via a cable or wireless link so that accomplishment of the dyslexia screening test, performed under the control of the headset firmware 64. Administration of the test is controlled through the control panel software application 65. Additional information is noted for patient health records and for billing records through the electronic medical records (EMR) software application 66. Also, the hospital system 63 may facilitate communication across a network, such as the Internet 67, to a remote processing facility, depicted as a data repository computer 68. Analysis using the classifier software application 69 may be performed remotely on the researcher computer 70 or an analysis computer 71. Users of the ERP screening system 62 may access the system 62 through research or computer 70 for the purpose of creating testing protocols with the control panel software application 65 or visualizing testing results using viewer software application 72. Users of the ERP screening system 62 may access the system 63 for the purpose of evaluating patient tests through physician (specialist) computer 73. Users may also store data on a database 74 connected to their own computers 70 and 73. Administrators of the system 62 may have direct access to the system database on data repository computer 68 through management console software application 75.

The data repository computer 68 and analysis computer 71 allow for the most up-to-date waveform recognition techniques to be employed to diagnose a neurological (e.g., dyslexia) condition. Moreover, the analysis computer 71 may process a number of data from screening tests to make such analysis more cost effective. Moreover, historical data may be mined as recognition techniques improve to capture previously undiagnosed conditions or to otherwise correlate previous test results with other forms of data to further refine the diagnostic process. It should be appreciated that the analysis performed by the analysis computer 71 could further include neural net processing, wherein the neural net is trained to recognize a waveform characteristic of dyslexia or other conditions.

Positive, inconclusive, and/or negative screening test results may be forwarded to an appropriate recipient, such as a referral physician 76 for further diagnostic testing and/or therapeutic measures.

Figure 8:
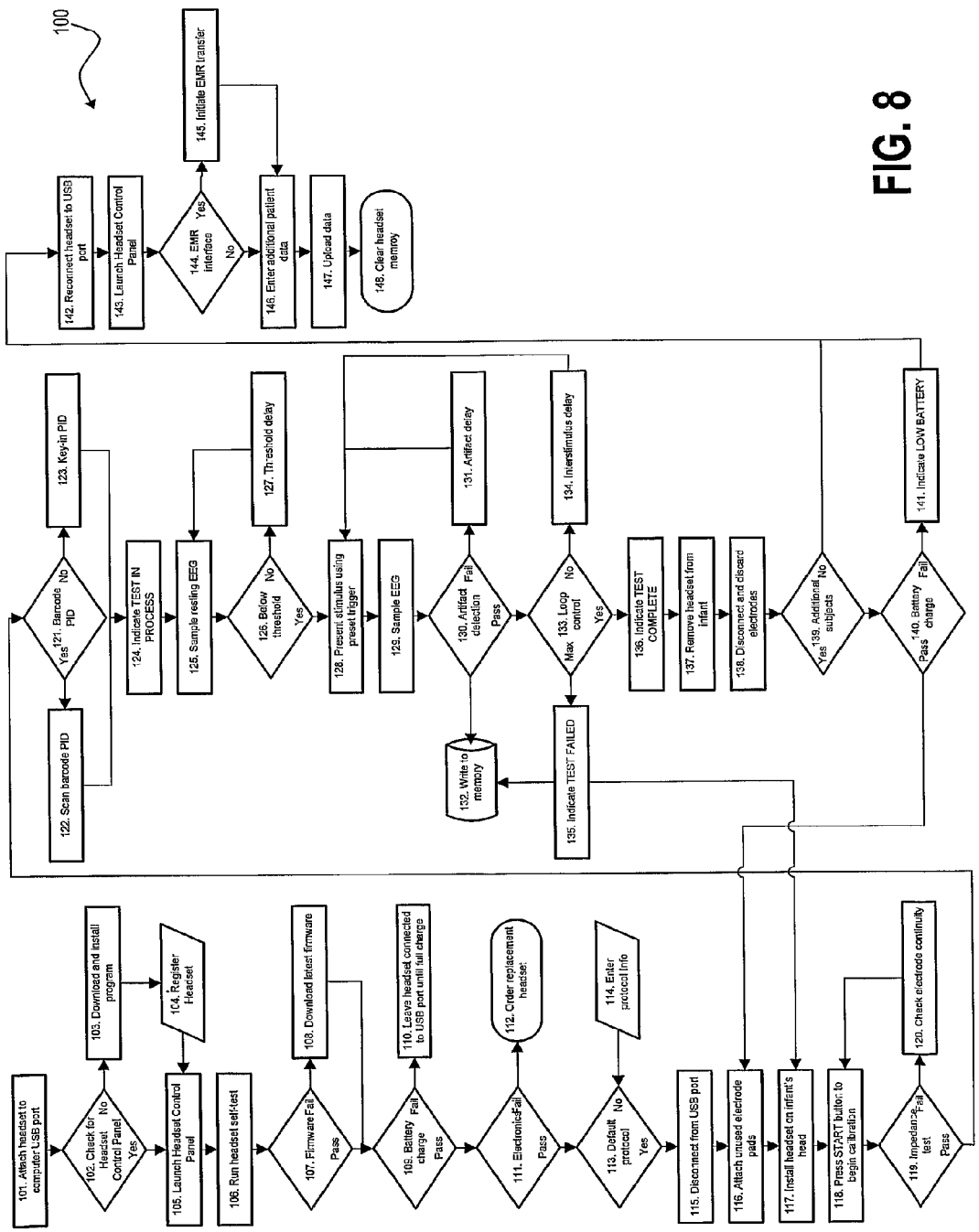
FIG. 8 is a flowchart describing a procedure or sequence of operations performed by the ERP headset of FIG. 1 to stimulate, capture, and analyze ERPs.

FIG. 8 depicts an illustrative procedure or sequence of operations 100 for ERP (e.g., dyslexia) screening performed by the test system 62 of FIG. 7. In block 101, the headset is attached to a computer USB port. If determined that the headset control panel indicates the need for initializing the headset (block 102), then a headset program is downloaded and installed (block 103) and the headset identification number and initialization status is registered (block 104). If initialization is not needed in block 102 or after registering in block 104, then the headset control panel is launched (block 105) and a self-test is performed by the headset (block 106). If the firmware is determined to have failed (block 107), then the latest firmware may be downloaded (block 108). If the battery is determined to have failed a charge test (block 109), then the headset is left connected to the USB port until fully charged (block 110). If the electronics self-test fails (block 111), then an indication is given to the user or electronically transmitted back via the USB port to order a replacement headset (block 112). If the user inputs that default protocol is not to be used (block 113), then the headset receives protocol information from the user, perhaps input through the control box or from a PC interface (block 114). In block 115, the headset is disconnected from a hospital computer or other device after a previous upload of screening test data, download of an updated test protocol, and/or charging of the batteries in the headset. The headset is prepared for the next subject by ensuring that the headset is sterile and has operable electrodes. One way is as depicted in block 116 by attaching an unused electrode pad to each of the electrode arms.

With the headset ready, the headset is placed upon an infant subject's head. The frame of the headset simplifies placement by including ear cups and a forehead frame to be aligned with the subject's eyebrows that intuitively guide the clinician in proper placement (block 117). This includes properly positioning reference electrodes at the patient's cheeks, although other predetermined reference locations may be selected, such as the forehead. Simplified initiation of the test is provided by depressing the start button on the attached control box (block 118). The headset interprets this button push and initiates a self-test to verify good reception of an EEG signal from the subject (e.g., impedance test) (block 119). The self-test is indicated on the headset indicator LED lights or control box. If failed, the clinician removes the headset from the infant's head and checks electrode continuity (block 120), which may entail visually checking for good electrode contact and/or reconnecting the headset to a hospital device to evaluate the cause of the failure. For instance, the headset may provide a more detailed explanation of the failure over the interface.

If in block 106 the self-test was deemed a pass, then a determination is made as to whether a machine readable patient identification (PID) such as a barcode is available (block 121). If so, the clinician uses the scanning device to scan in a PID code from the subject (block 122), else the PID is manually keyed in (block 123). The headset responds by giving an indication of a test in process so that the clinician leaves the headset undisturbed (block 124). Then, the headset samples resting EEG at the various electrodes (block 125), This sampling includes making a determination whether an EEG voltage is below a threshold indicative of a resting, unstimulated state (block 126), and if not, a threshold delay is imposed (block 127), looping back to block 125. Else, if the appropriate initial condition is found in block 126, then a stimulus is presented using a preset trigger defined by the protocol (block 128). The EEG is then sampled at the appropriate combination of electrodes and at a sample rate appropriate for the frequency of interest (block 129).

Another feature that may enhance consistent results is defining an initial starting point on the same slope of a detected resting brainwave (e.g., rising slope, falling slope, apex, nadir).

Advantageously, the headset performs a data integrity check, such as by comparing the sampled data against various criteria to detect artifacts indicative of noise or external stimuli that corrupted the data sample (block 130). If detected, then an artifact delay is imposed (block 131) before looping back to block 128. Else, the data samples are written to memory in the headset (block 132), including storing the PID for tagging to the screening test data. Typically, the test protocol includes a series of stimuli and samples. Thus, a determination is made that another control loop is to be performed (block 133). If so, an appropriate interstimulus delay is imposed to return to a resting EEG (block 134) followed by looping back to block 128. However, if more control loops are warranted but a threshold is exceeded for a maximum time or a maximum number of attempts, then the test failed indication is given (block 135) and the procedure returns to block 117 for the clinician to reposition the headset for retesting. If, however, in block 133 the inner and outer control loops that define the testing protocol are deemed complete, then a test complete indication is given to the clinician (block 136), such as by illuminating an appropriate LED light.

If test complete is determined in block 136, then the headset is removed from the infant subject's head (block 137) and the used electrode pads are removed and discarded from the headset (block 138). If another subject is to be tested prior to uploading screening test data (block 139), a battery charge check is made (block 140) to see if the remaining charge is sufficient. If it passes, then processing loops back to block 116 to prepare the headset for the next subject. If failed, then a low battery indication is given (block 141).

If no additional subjects are determined in block 139 or if low battery is determined in block 141, it is time for reconnecting the headset to the USB port of the hospital computer (block 142), which recharges the headset and also provides an opportunity to activate an Internet connection to initiate data upload and any new test protocol download. In particular, a headset control panel is launched for interacting with the clinician (block 143). If an electronic medical record (EMR) interface is determined to be available (block 144), then an EMR transfer is initiated (block 145). If EMR transfer is not available or after EMR transfer is initiated, then the clinician is afforded an opportunity to enter additional patient data (block 146). The data is uploaded to the ERP system (remote user) for analysis and disposition (block 147) and the headset memory cleared for the next use (block 148).

For instance, the remote user may perform diagnostic analysis on the received screening test data to see if the ERP data is indicative of dyslexia. If a determination is made that the results are not positive for dyslexia, then the appropriate recipient is informed, such as the parent or the attending pediatrician or obstetrician. If positive, then the test results may be advantageously forwarded to an in-network referral physician, such as a child psychologist.

Figure 9:
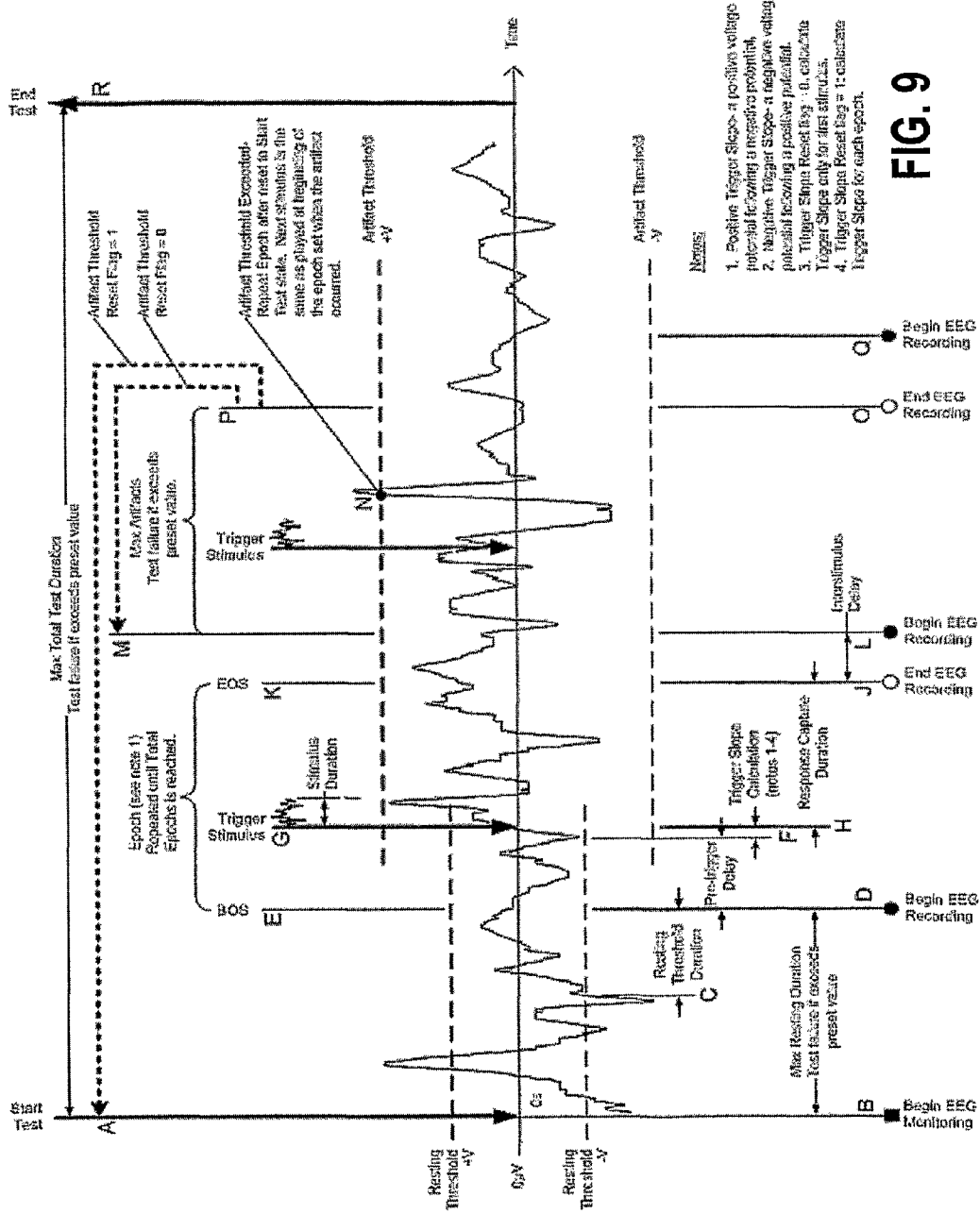
FIG. 9 is a graph of an ERP as a function of time illustrating an automated screening control schema for ERP testing.

In FIG. 9, a timing chart illustrates a sequence of events involved in an ERP test. At time "$T_A$" the test subject's barcode wristband is scanned and the test begins. Concurrently, the headset begins monitoring the brainwaves at time "$T_B$" to identify when the amplitude of the resting brainwaves falls below the preset resting threshold at time "$T_C$" and remains there for a preset duration. This begins the recording of the brainwaves at time "$T_D$". This point is called beginning of series (BOS), at time "$T_E$". Next, the headset calculates the slope of each subsequent brainwave at time "$T_F$" and triggers the stimulus when the slope criteria is met at time "$T_G$" beginning a response capture period at time "$T_H$". The stimulus is generally of short duration at time "$T_I$". At the end of the response capture period, the brainwave recording stops at time "$T_J$". For a single stimulus series, this is called end of series (EOS) at time "$T_K$". Time sequence from time "$T_E$" to time "$T_K$" defines the first epoch. A predetermined interstimulus delay passes at "$T_L$" before the next epoch at time "$T_M$" is begun. During the next epoch, the chart shows an artifact where the amplitude of the recorded brainwave exceeds the artifact threshold at time "$T_N$". At the end of this epoch the EEG recording stops at time "$T_O$" and the sequence is redirected at time "$T_P$" back to the beginning of series at time "$T_M$" if the artifact threshold reset flag is set to "1" or to before the resting threshold at time "$T_A$" if the flag is set to "0". If the artifact threshold is not exceeded, a new epoch is begun at time "$T_Q$". The test ends when all epochs are completed or when the total test time is exceeded at time "$T_R$".

In FIG. 10, an illustrative stimulus library is depicted having seven general types of stimulus, representing the kind of auditory stimuli that can be downloaded into headset memory to be used to evoke a brainwave response. Any recorded, or synthesized audio stimulus may be used with this list being merely exemplary. In particular, the library may include a click that is of a narrow frequency band of extremely short time duration (i.e., spike). A burst is a broadband signal of short duration. A pip/chirp is a single frequency on a half-cycle carrier. A steady-state tone is a single frequency, constant amplitude stimulus. A master is a single frequency, continuous cycle stimulus. A phoneme is a single-phoneme speech sound stimulus. A word is a word stimulus.

In FIG. 11 an illustrative table is depicted which lists the kind of sequences that can be downloaded into the headset memory to be used to evoke a brainwave response. In particular, the library may include a repetition stimulus which repeats a single stimulus. A steady state is a single tone of long duration. An equal probability sequence repeats multiple stimuli an equal number of times. Match-mismatch is a pair of stimuli presented with minimal interstimulus delay and which either match or do not match. Odd ball is a single standard stimuli with one or more deviant stimuli. Variable frequency is a constant volume stimulus of varied frequency. Variable volume is a constant frequency stimuli of variable volume. Variable time warp is a constant tone stimulus of varied duration. User defined is a user defined sequence presentation of volume, tone and time warp.

In FIG. 12 an illustrative table is depicted which lists data capture settings that may be accessed, selected, modified, or otherwise utilized by the headset 10 to adapt its testing capabilities. For instance, a range of preset electrode locations may be configurable, for example 10 to 20 locations identified by an electrode location label. For instance, a selected headset 10 with its choice of cantilevered arms and electrode placements may use a subset of available locations. However, the system is capable of being used with different locations. Electrode selection specifies which electrode locations will be selected for data capture. Data capture start and end defines what latency is expected for the brainwave of interest. Data capture rate sets what rate the system should sample the electrodes to capture data. Signal gain sets amplification as appropriate for the particular electrode location, brainwave of interest, and perhaps a detected impedance/resting brainwave pattern. In addition, artifact detection parameters may be advantageously incorporated so as to determine if a particular ERP test did not receive an undisturbed result. This artifact detection may be a voltage threshold that should not be exceeded during the data sampling.

Figure 13:
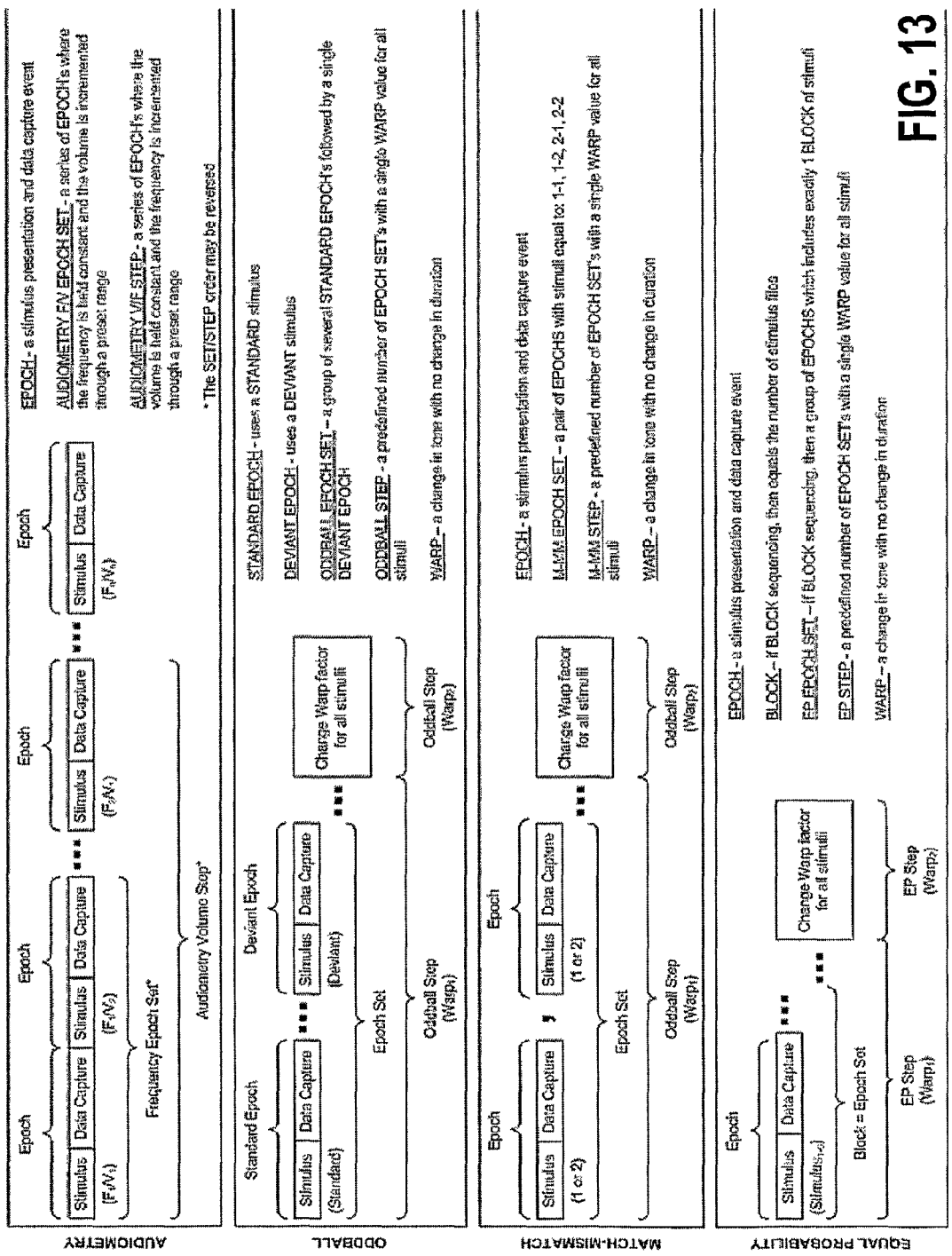
FIG. 13 is a diagram illustrative of the ERP protocol hierarchy for; audiometry testing, an ERP oddball paradigm, an ERP match-mismatch paradigm, and an ERP equal probability paradigm performed as part of ERP screening system of FIG. 7.

In FIG. 13 an illustrated table is depicted which shows the order, grouping, and grouping hierarchy of stimuli for various protocol paradigms used by the integrated ERP headset 10 to detect an ERP. Such protocol paradigms including audiometry, oddball, match mismatch, and equal probability may be performed as part of the procedure 100 of FIGS. 8 and 9.

Three levels of stimulus hierarchy are described in FIG. 13. The first level is an "epoch" which is always used to refer to the sequence of steps shown in FIG. 9 step E-J including; start recording, inter-stimulus delay, present stimulus, capture the ERP, and stop recording. A paradigm-specific logical grouping of epochs called an "epoch set" is also described. The highest grouping level is a "step" which generally defines a group of epoch sets which will be repeated exactly except for a single change in a stimulus parameter such as warp (a change in pitch without a change in duration) across all epochs.

In an audiometry paradigm, epoch sets are defined as a series of epochs where either the frequency is held constant and the volume is incremented through a preset range or the volume is held constant and the frequency is incremented through a preset range. An audiometry step is a repeat of the previous epoch set with a change in the fixed parameter, either volume of frequency. Thus, the audiometry frequency/volume set/step paradigm increments through a preset range of frequency and volume combinations, thereby, the subject's hearing sensitivity at various frequencies is determined.

In an oddball paradigm, epochs are defined as "standard" whereby it includes a stimulus which are presented a majority of the time or "deviant" whereby it includes a different stimulus which are presented a minority of the time. An oddball epoch set is defined as several standard epochs followed by a single deviant epoch. An oddball step is the repeat of a group of oddball epoch sets with a change in a single stimulus parameter such as warp (a change in pitch with no change in duration).

In a match-mismatch paradigm, an epoch set is defined as a pair of epochs in which the stimulus in each epoch is either the same and matches or is different and is a mismatch. A match-mismatch step is the repeat of a group of match-mismatch epoch sets with a change in a single stimulus parameter such as warp (a change in pitch with no change in duration).

In an equal probably paradigm, an epoch set is defined as a predetermined number of epochs each with a different stimulus. Subsequent epoch sets will have the same number of epochs as the previous epoch set with the same stimuli but potentially in a different order. An equal probability step is the repeat of a group of equal probability epoch sets with a change in a single stimulus parameter such as warp (a change in pitch with no change in duration).

FIG. 14 is an illustrative diagram which shows the grouping of stimuli for various ERP paradigms used by headset 10 whereby each lower case letter "a", "b", "c", and "d" represents a different stimulus and these lower case letters "a", "b", "c", and "d" separated by dashes ("-") represent the sequence of stimuli used in an ERP test. Additionally, the grouping of lower case letters "a", "b", "c", and "d" designated by a horizontal arrow ("⇋") denotes an epoch set.

In particular, an oddball paradigm is shown whereby the lower case letter "a" represents a standard stimulus and the lower case letters "b" and "c" represent deviant stimuli. In this illustrative example the first epoch set is the sequence of stimuli "a-a-a-b", the second epoch set is "a-a-a-b", and the third epoch set is "a-a-a-c".

Additionally, a match-mismatch paradigm is shown whereby two stimuli, "a" and "b" are presented. The first epoch set "a-b" represents an "a" mismatch, the second epoch set represents an "a" match, the third epoch set "b-a" represents a "b" mismatch, and the fourth epoch set "b-b" represents a "b" match.

Additionally, an equal probability paradigm is shown whereby four stimuli are four different stimuli are used; "a", "b", "c", and "d". Three epoch sets are shown represented by the three sequences; "a-b-c-d", "c-a-d-b", and "b-d-a-c". In this illustrative example, the four stimuli "a", "b", "c", and "d" are randomly distributed within each epoch set. This distribution of stimuli is called block random distribution.

Figure 15:
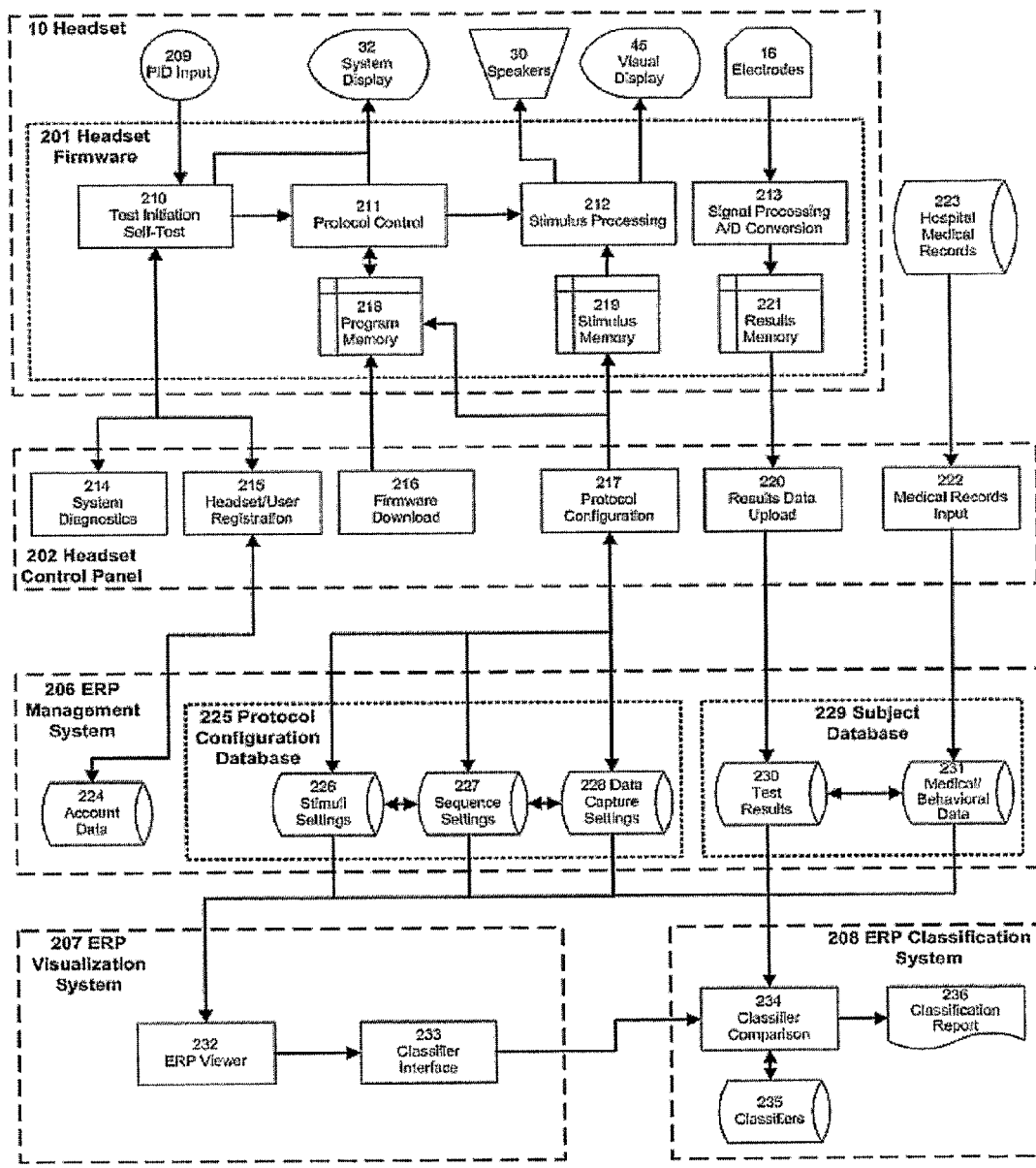
FIG. 15 is a diagram of the software modules and information flow through the ERP screening system of FIG. 7.

FIG. 15, depicts a system to program an ERP headset, perform an ERP test, upload the test data, view the test data, and perform an analysis and classification. The headset (block 10) contains input/output devices including a patient identification means (block 209), a system status display (block 32), sound projectors (block 30), a visual stimulus display (block 45), and electrodes (block 16). The headset (block 10) is controlled through on-board firmware (block 201) which performs functions such as test initiation and self-test (block 210), protocol control (block 211), stimulus preprocessing (block 212), and signal processing and A/D conversion (block 213). The headset (block 10) is programmed through a web-enabled headset control panel application (block 202). The headset control panel (block 202) communicates with the headset firmware (block 201) to perform a system diagnostic (block 214), register the headset and any users (block 215), to download the latest firmware (block 216), to configure the desired test protocol (block 217) and load those protocols and stimulus data into the headset memory (block 218 and block 219 respectively), upload test results (block 220) from the test result memory (block 221), and input medical record information (block 222) from a hospital medical record database (block 223). The headset control panel (block 202) also communicates with the ERP management system (block 206) which contains an account database (block 224), a protocol configuration database (block 225), and a subject database (block 229). The protocol configuration database (block 225) stores protocol information such as stimulus settings (block 226), stimulus sequence settings (block 227), and the data capture settings (block 228). The subject database (block 229) stores all ERP test results (block 230) and any medical or behavioral data (block 231) about the subject being tested. Testing results (block 230) may be viewed on a computer using the ERP visualization system (block 207) which includes two modules for viewing the ERP waves (block 232) and for inputting various settings (block 233) for the ERP classifier application (block 234). The ERP classifier (block 234) compares subject test results (block 230) resulting from a specific testing protocol (block 225) against a database of known classification templates (block 235) and then generates a classification report (block 236).

Figure 16:
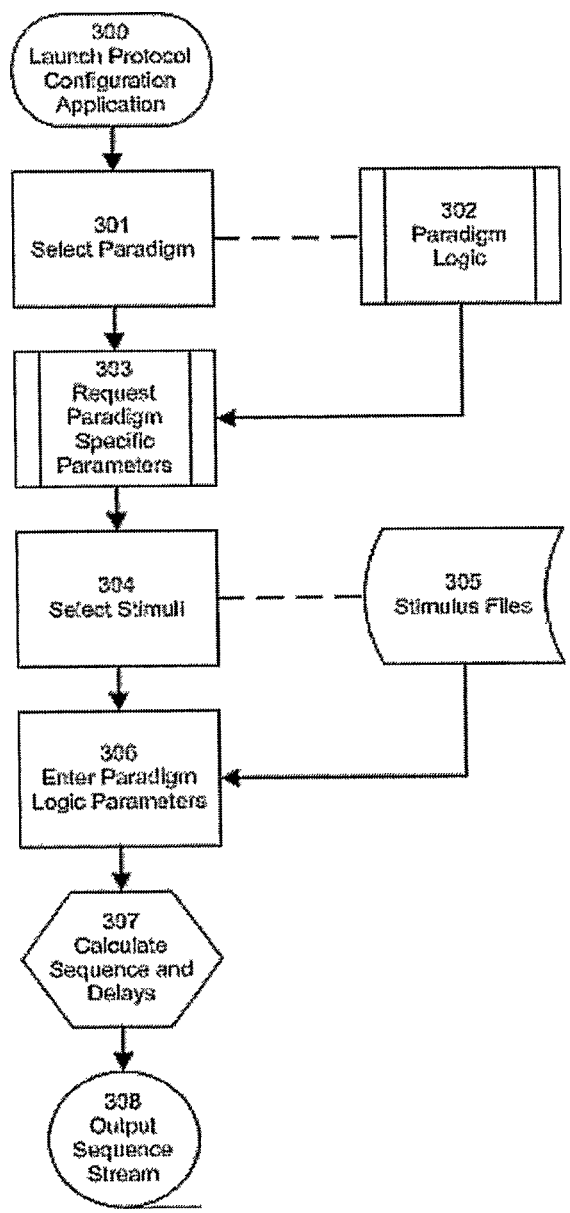
FIG. 16 is a diagram illustrative of the logical process performed by a protocol configuration module of a headset control panel of the ERP screening system of FIG. 7 that generates a stimulus sequence.
Figure 19:
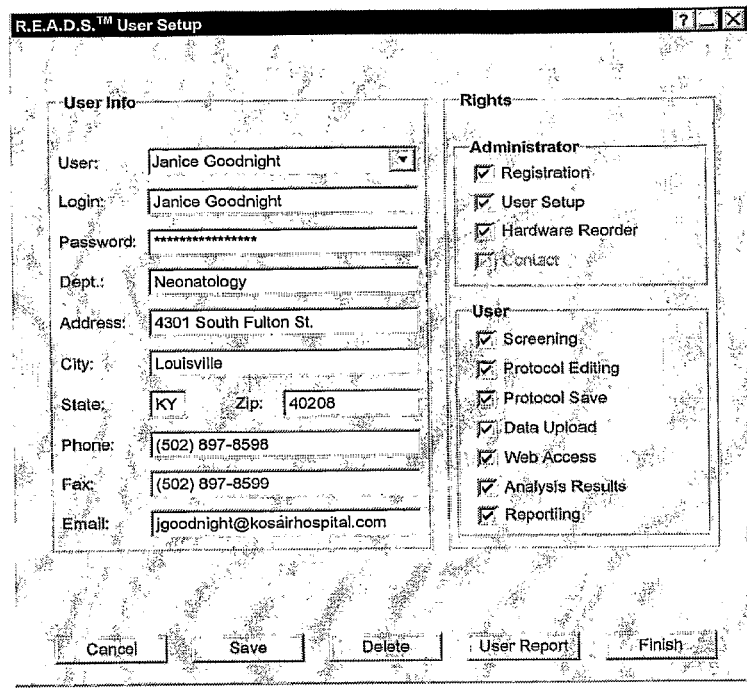
FIG. 19 is a depiction of a GUI for user setup for an ERP headset of the ERP screening system of FIG. 7.
Figure 20:
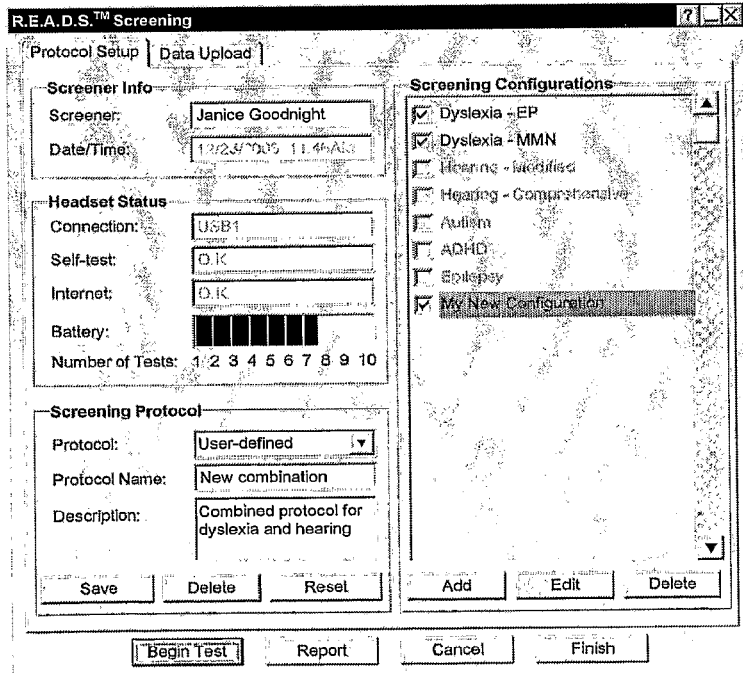
FIG. 20 is a depiction of a GUI for screening protocol setup for an ERP headset of the ERP screening system of FIG. 7.

FIG. 16 depicts the logical process performed by the protocol configuration module (block 217) of the headset control panel (block 202). Once the protocol configuration module (block 217) has been invoked (block 300), the user is prompted to select a specific ERP paradigm (block 301) from the protocol configuration database (block 225). Information within the protocol configuration database (block 225) describes the paradigm logic used to determine stimuli sequence (block 302). The user is then prompted to enter the paradigm-specific parameters (block 303). These parameters could include "number of stimuli to use", "block grouping method", or "inter-stimulus delay". The user is then prompted (block 304) to select the desired stimuli (block 305) from the stimulus library (block 226). The user is then prompted for stimulus-specific parameters (block 306) such as "volume". Once all protocol configuration parameters are entered, the stimulus sequences are generated along with the timing of each stimulus presentation (block 307). Upon saving the aforementioned protocol configuration and settings, a data stream (block 308) composed of the stimuli, sequencing, and timing may be downloaded into the headset 10.

In FIGS. 17-23, a series of graphical user interface (GUI) depictions are given to illustrate how a clinician interfaces with the ERP screening system in order to use the ERP headset 10.

In use, a headset 10 advantageously integrates sound projectors (earphones) 28 and flexible electrode arms 18, 18' that easily and accurately position electrodes 16 on a patient's scalp. A recurved headset frame 14 ensures the proper angle between ear cups 26 as well as providing a convenient ability to position the headset with a supine subject at the brow of the subject. Flex circuitry incorporates networked electrodes within an economical assembly. The contact points of the headset 10 may advantageously include fluid-filled bladders that provide comfort, a good seal for excluding noise from ear cups 26, and uniform impedance at electrodes 16. A digital control box 41 contains a microprocessor, battery, and a patient ID system (e.g., barcode or RFID scanner) in order to perform the auditory testing conveniently in a clinical setting. Samples are taken from each electrode 16, 16', 16" at an appropriate data rate for the appropriate frequency and duration to reduce data storage file size. Automatic detection of artifacts causes replay of affected epochs to avoid failed tests. Different audio tests (e.g., audiometry, mismatched negativity, equal probability) are supported by PC-based programming system that connects to a web-based database for downloading/modifying testing protocol configurations for loading onto headset. A particularly advantageous protocol is supported by randomizing stimulus sequences, which is used when presenting multiple stimuli when each needs to be repeated an equal number of times in random order. Data integrity is maintained by performing artifact detection and resting threshold monitoring before initiating stimulus based upon the slope of the resting brainwaves.

Figure 24:
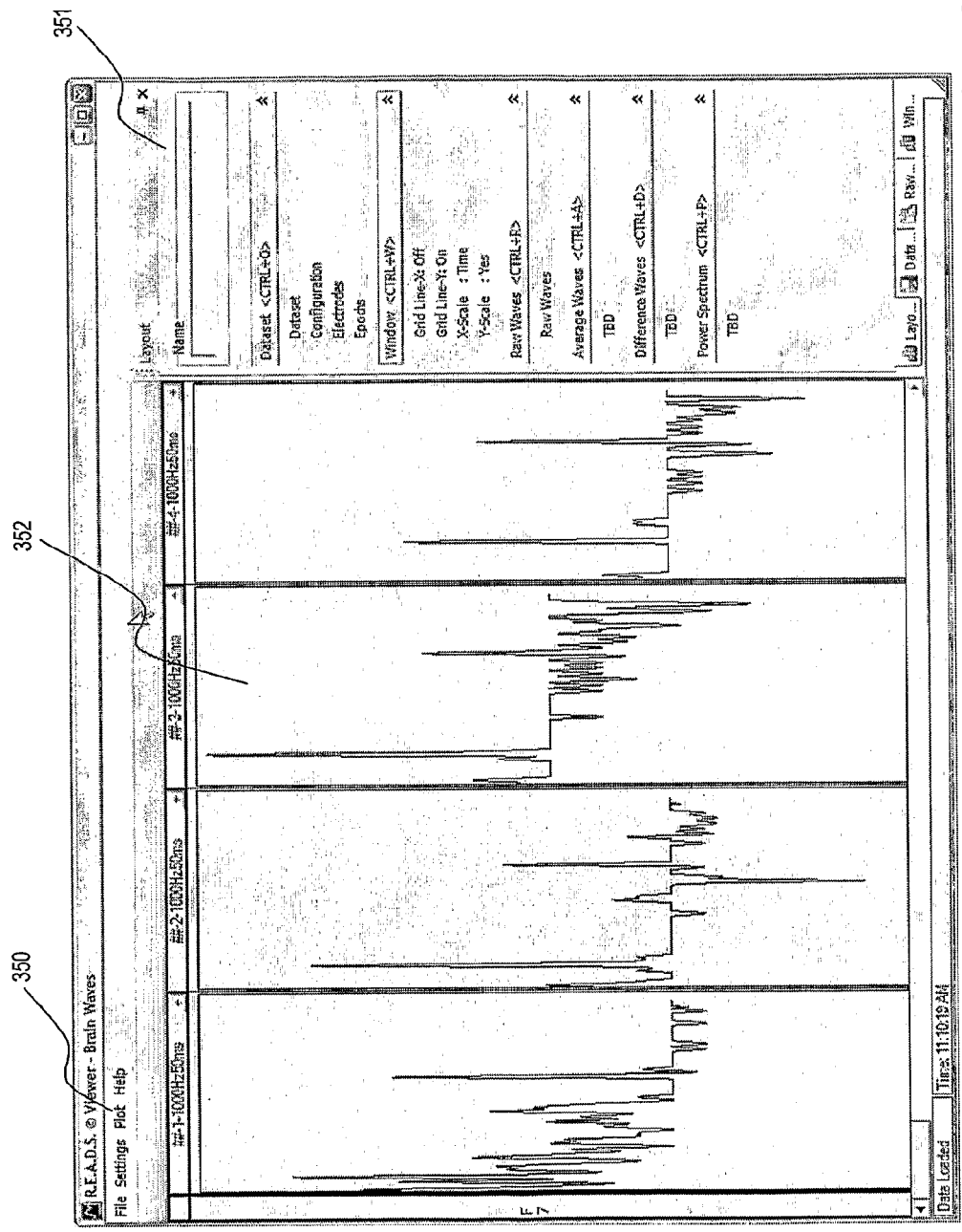
FIG. 24 is a depiction of a GUI for a software application to view the results of the ERP test of FIG. 8.

In FIG. 24, a depiction of a graphical user interface (GUI) is shown which illustrates how a clinician or researcher interfaces with the ERP visualization system (block 207) to visualize the ERP data from an ERP test described in FIG. 8. The interface includes a menu bar 350 which contains a list of commonly used commands such as to open a file. A settings panel 351 is also shown which contains a list of context sensitive, commonly used settings such as line color. The display window 352 displays graphical representations of the ERPs from the ERP test described in FIG. 8 based upon the selected settings from the settings panel 351.

Figure 25:
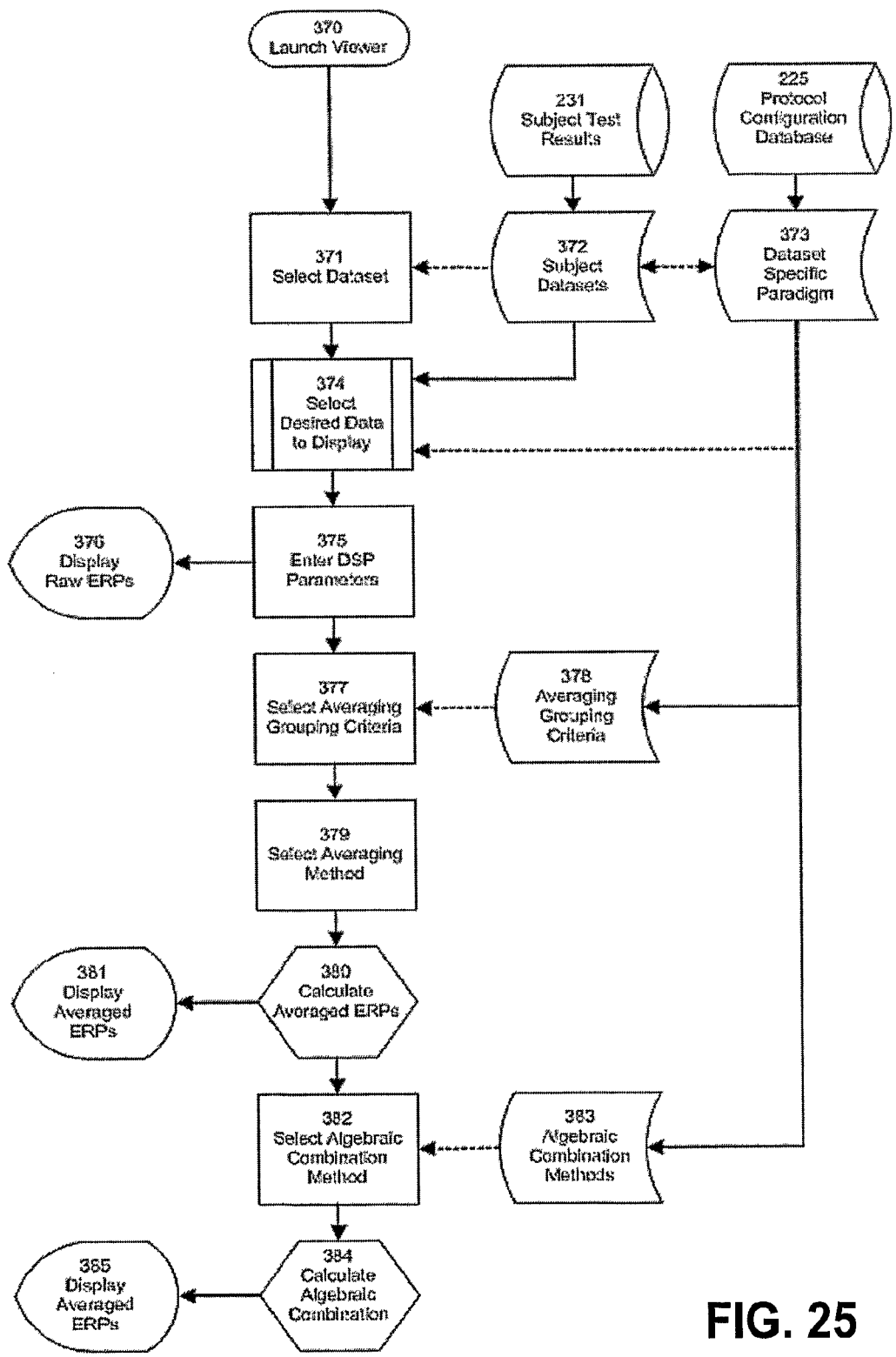
FIG. 25 is a diagram illustrative of the logic used by the ERP visualization system of FIG. 24.

FIG. 25 depicts a system to advantageously select and process raw ERPs from tests described in FIG. 8 for visualization using an ERP visualization system (block 207). Once an ERP test as shown in FIG. 8 is completed and the data has been uploaded to the database server (block 98), a user launches (block 370) an ERP visualization system (block 207) and selects a dataset (block 371) from a specific subject ERP test (block 372) which has been stored in the subject test results database (block 231). The selected dataset (block 371) is related to the paradigm (block 373) used to create the dataset (block 371) through a reference to the protocol configuration database (block 225). The paradigm-specific information (block 373) is used to describe various aspects of the data (block 373) including the number tests, performed, how each test was performed, etc. Once a dataset (block 371), which may contain multiple data, has been selected, the user then selects which data is to be displayed (block 374). As an example, this could include various paradigm-specific (block 373) logical groupings of the data such as only data from deviant stimuli in an oddball paradigm (FIG. 14), or only data from a subset of the total number of electrode channels. After the desired data has been selected (block 374) the user may manipulate the data using various digital signal processing functions (block 375) such as band pass filtering, amplitude normalization, or slope normalization. The data, which are individual ERP waves, may then be displayed on a computer screen (block 376). In order to increase the signal to noise ratio of the ERPs, which will be required for subsequent data analysis, it is desirable to create an approximation of a large group of ERPs which have been evoked in the same manner and which derive from epochs at equivalent logical locations within an ERP sequence. This requires selecting ERPs (block 377) based on their paradigm-specific logical grouping criteria (block 378) which derives from the stored relationships to the protocol configuration database (225). The user then selects an ERP averaging method (block 379) such as linear averaging or nonlinear alignment averaging. Whereupon an ERP visualization system (block 207) automatically performs the averaging calculations (block 380) and displays (block 381) an approximation of the raw ERPs. In certain ERP paradigms, such as the oddball paradigm of FIG. 14 used in mismatch match negativity (MMN) experiments, the averaged ERPs require additional manipulations such as performing an algebraic combination of the ERPs. In MMN experiments, the averaged ERPs from deviant epochs are subtracted from the averaged ERPs from standard epochs. The result of this process is an ERP approximation of the differences in neural processing of standard and deviant stimuli. In an ERP visualization system (block 207), whereupon the desired averaged ERPs have been approximated (block 380), a user may then select an algebraic calculation method (block 382) from a list of appropriate methods for the specific paradigm (block 383). The algebraic calculations are then performed (block 384) and the resultant ERPs are displayed (block 385).

Figure 26:
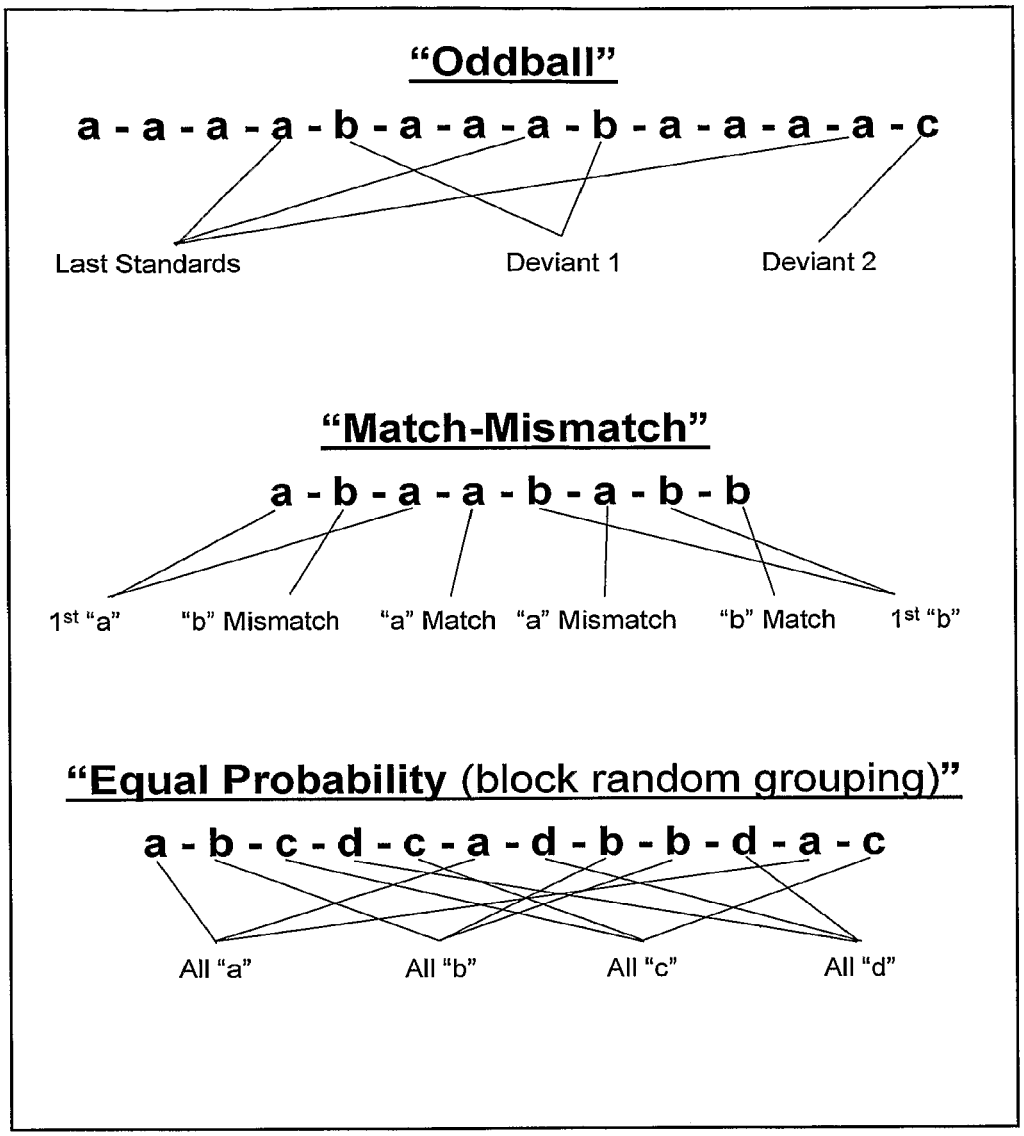
FIG. 26 is a diagram illustrative of the averaging logic used by an ERP visualization system of of FIG. 24.

FIG. 26 is an illustrative diagram which shows the paradigm-specific averaging logic used by an ERP visualization system (block 207) where the lower case letters "a", "b", "c", and "d" represent different stimuli used in an ERP sequence. In an oddball, match-mismatch, or equal probability paradigm, it is often advantageous and desirable to group ERPs based on the stimulus used to evoke the ERP and the location within the stimulus sequence where a particular ERP would be evoked.

In the oddball example shown, an ERP visualization system (block 207) may optionally group all epochs which contain a standard stimuli "a" in the temporal location just preceding a deviant stimulus such as "b" or "c". All epochs containing a deviant stimulus "b" may also be grouped Likewise, all epochs containing any other deviant stimulus such as "c" may be grouped.

In the match-mismatch example shown, an ERP visualization system (block 207) may optionally group all epochs with the same stimuli "a", "b", or other, in the first temporal location within a match-mismatch stimulus pair. Additional groupings of epochs related to the second stimulus in the match-mismatch stimulus pair may also be performed such as the "b" mismatch, "b" match, "a" match, and "a" mismatch groups. If more than two stimuli are used, additional groups depending on whether the stimuli pair match or do not match can be performed.

In the equal probability example shown, an ERP visualization system (block 207) may optionally group all epochs which contain the same stimuli, such as all "a" epochs, "b" epochs, "c" epochs, and "d" epochs.

Figure 27:
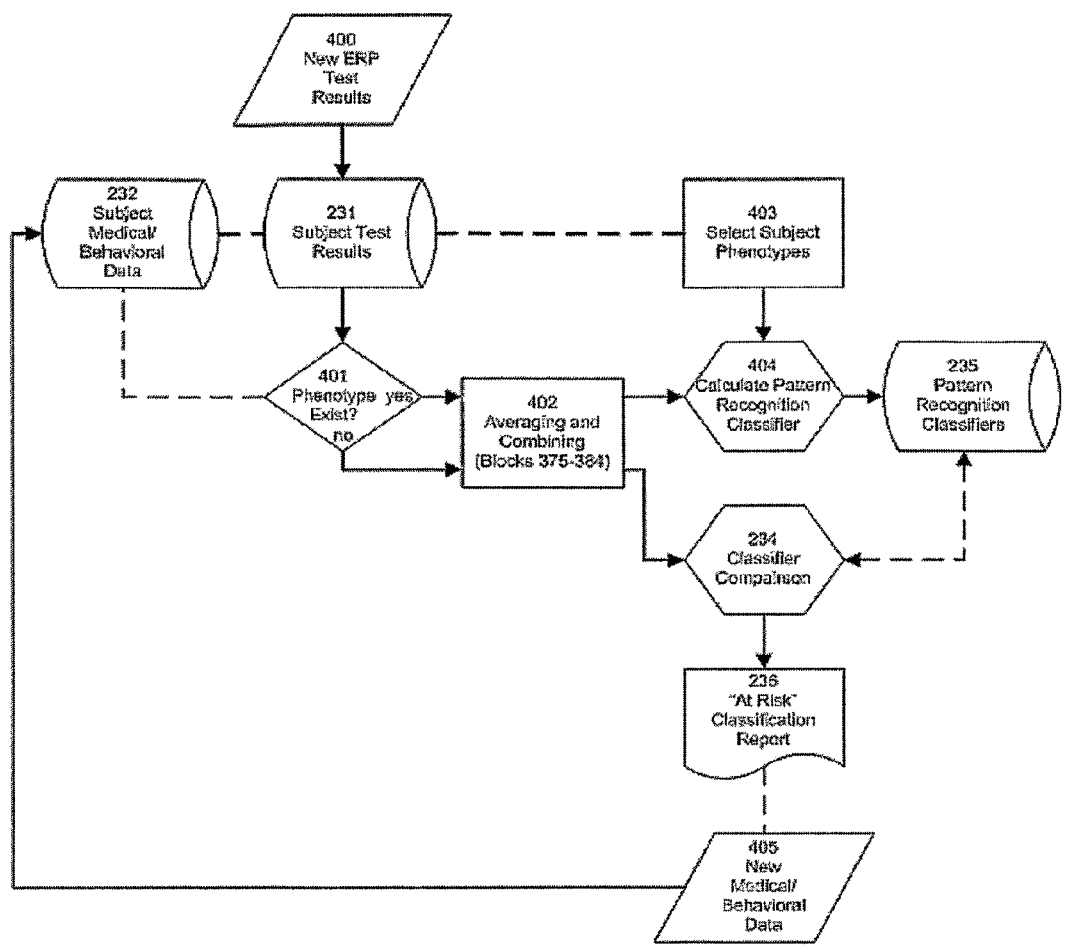
FIG. 27 is a diagram of logic for creating pattern recognition classifiers and for comparing new ERPs to the classifiers for the purpose of performing a predictive diagnosis using an ERP classification system of the ERP screening system of FIG. 7.

In FIG. 27 is an illustrative diagram which shows the logic for creating pattern recognition classifiers and for comparing new ERPs to the classifiers for the purpose of performing a predictive diagnosis using an ERP classification system (block 208).

New ERPs are captured (block 400) using an ERP system FIG. 7. The ERPs are uploaded to a subject test results database (block 231). If medical or behavioral data about the test subject (block 232) which can describe a particular phenotype of interest (block 401) exists, then the ERPs (block 231) are averaged and combined (block 204) using steps (block 375-384). The averaged ERPs, along with a phenotype identifier, are then used to train (block 404) the pattern recognition classification system (block 234) to detect the phenotypes of interest. The classifiers are then stored in the pattern recognition classifier database (block 235) for later use.

If the new ERP subject test results (block 400) do not include medical or behavioral data and are to be used to perform a classification (block 234) then the ERPs (block 231) are averaged and combined (block 204) using steps (block 375-384) and then are classified (block 234) and a classification report (block 236) is created.

If, at some later time, new medical or behavioral data which could correlate with a particular subject phenotype (block 405) is generated, the subjects original ERPs (block 400) can then be used to begin a new classifier training loop (blocks 231, 231, 401, 402, 404, and 235). This feedback loop has the advantage of constantly improving the classification accuracy and performance of the ERP classification system (block 208).

Figure 28:
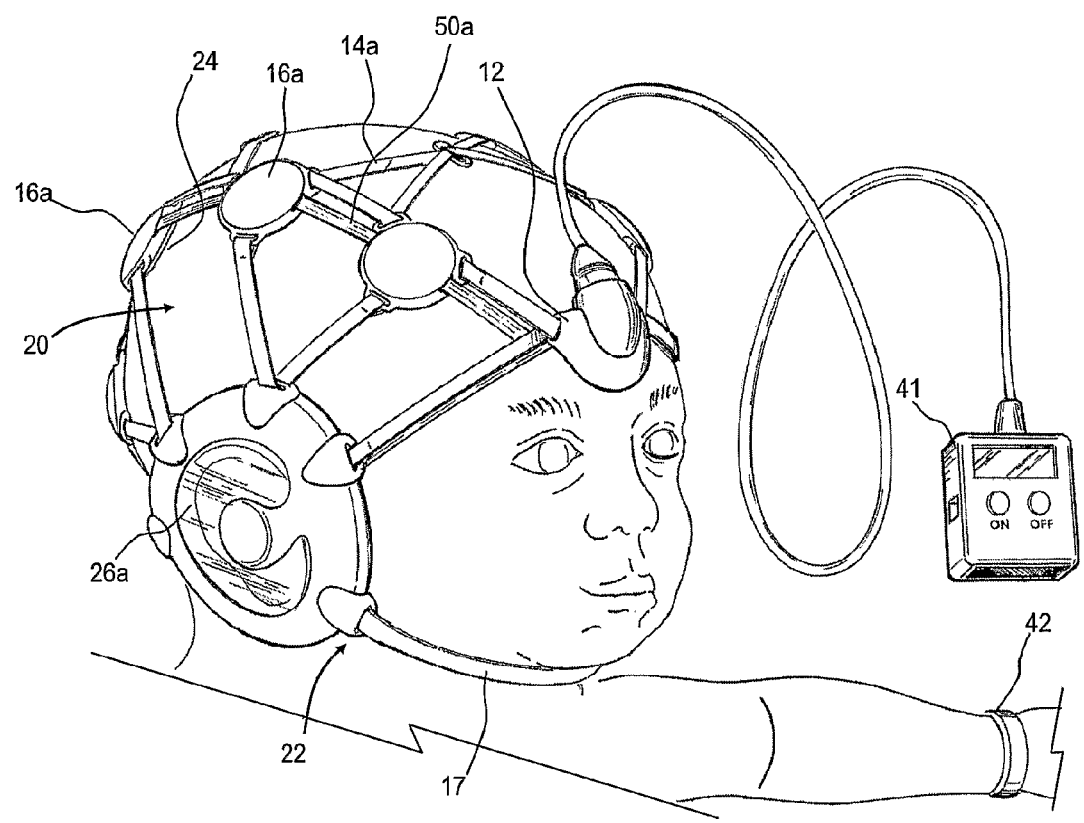
FIG. 28 is a perspective view of an alternative headset with flexible straps for the ERP screening system of FIG. 7.

In FIG. 28, an alternative headset 10' includes ear cups 26a and electrodes 16a that are electrically connected by a flex circuit 50a and flexibly connected by elastic bands 14a with a chin strap 17 for enhanced retention.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, although a headset 10 is described herein for use with infants, it should be appreciated that applications consistent with the present invention may be used on older children and adults. Moreover, whereas evoked response testing has many advantages, it may be desirable to incorporate manual responses from a subject, such as depressing a button in response to hearing or seeing a stimulus.

For example, although a headset 10 and distributed dyslexia screening system 70 have been illustrated that have certain advantages, all of the functionality may be incorporated into a headset. Alternatively, a disposable headset may be used with most of the active components and processing connected thereto. As yet a further alternative, a general-purpose computer may be configured to perform the testing protocol and/or the waveform analysis with the headset including essentially only electrodes and speakers.

As another example, although screening of infants is advantageously emphasized herein, older children and adults may be advantageously tested as well.

As yet an additional example, although dyslexia is a condition discussed herein, it will be appreciated that other neurological conditions may advantageously be tested by a similar headset with a frame positioning electrodes in a desired position and configuration and using a similar ERP paradigm and protocol. Examples include autism, hearing loss, schizophrenia, Alzheimer's, etc.

For example, although a headset 10 and distributed ERP screening system 62 have been illustrated that have certain advantages, all of the functionality may be incorporated into a headset. Alternatively, a disposable headset may be used with most of the active components and processing connected thereto. As yet a further alternative, a general-purpose computer may be configured to perform the testing protocol and/or the waveform analysis with the headset including essentially only electrodes and speakers.

As another example, although screening of infants is advantageously emphasized herein, older children and adults may be advantageously tested as well.

As yet an additional example, although dyslexia is a condition discussed herein, it will be appreciated that other neurological conditions may advantageously be tested by a similar headset with a frame positioning electrodes in a desired position and configuration and using a similar ERP paradigm and protocol. Examples include autism, hearing loss, schizophrenia, Alzheimer's, etc.

I claim:

1. A method of using an Evoked Response Potential (ERP) testing system to administer a test on a test subject, wherein the ERP testing system comprises a headset, the method comprising:
  (a) positioning the headset on the head of the test subject, wherein the headset comprises:
    (i) a signal electrode,
    (ii) a reference electrode,
    (iii) a stimulus producer,
    (iv) a semi-rigid frame with a left ear cup and a right ear cup, wherein the semi-rigid frame is curved such that. as the semi-rigid frame flexes as a result of increasing the distance between the left ear cup and the right ear cup, the orientation of the left ear cup and the right ear cup do not change with respect to the head,
    (v) a control module contained within the semi-rigid frame, and
    (vi) a forehead frame configured to align with the eyebrows of the head, wherein aligning the forehead frame with the eyebrows results in proper placement of the plurality of electrodes;
  (b) providing the test subject with access to one or more buttons on the control module, wherein the control module further comprises:
    (i) a memory, wherein the memory stores a plurality of evoked response testing protocols including instructions for the stimulus producer, and
    (ii) a controller operably configured to actuate one of the plurality of evoked response testing protocols stored in the memory, wherein the controller is further configured to communicate a plurality of control administration parameters to the headset for performing an evoked response test;

(c) executing a selected one of the stored evoked response testing protocols though the headset via the controller, wherein all of the functionality required to perform the selected one of the stored evoked response testing protocols is included in the headset;

(d) receiving manual inputs from the test subject via the one or more buttons on the control module;

(e) receiving a stimulated EEG result via the signal electrode; and (f) recording data in the memory based on the manual inputs received from the test subject and the stimulated EEG result.

2. The method of claim 1, wherein the act of executing a selected one of the stored evoked response testing protocols though the headset via the controller comprises selectively activating the stimulus producer, wherein the act of receiving manual inputs from the test subject comprises receiving one or more manual inputs in response to one or more stimuli from the stimulus producer.

3. The method of claim 1, wherein the act of receiving manual inputs from the test subject comprises receiving a manual input to initiate the execution of the selected one of the stored evoked response testing protocols.

4. The method of claim 1, wherein the stimulus producer is operable to provide a visual stimulus to the test subject, wherein the act of executing a selected one of the stored evoked response testing protocols comprises providing a visual stimulus to the test subject via the stimulus producer.

5. The method of claim 1, wherein the stimulus producer is operable to provide an auditory stimulus to the test subject, wherein the act of executing a selected one of the stored evoked response testing protocols comprises providing an auditory stimulus to the test subject via the stimulus producer.

6. The method of claim 5, wherein the auditory stimulus is selected from a set of auditory stimulus files having characteristics that vary based on one or more of acoustic frequency, time duration, stimuli sequence, or time warp, wherein time warp denotes a selected sound stimulus having a lengthened duration and an unchanged pitch or changed pitch with unchanged duration.

7. The method of claim 1, wherein the plurality of control administration parameters are selected from a group consisting of a stimuli start time, a stimuli selection, a stimuli sequence, a failure determination, and sample mode.

8. The method of claim 1, further comprising coupling the control module with a remote storage system.

9. The method of claim 8, further comprising transmitting control administration parameters from the remote storage system to the control module.

10. The method of claim 8, further comprising transmitting data recorded in the memory from the control module to the remote storage system.

11. The method of claim 10, further comprising using the remote storage system to perform ERP diagnostic analyses on the data transmitted from the control module to the remote storage system.

12. The method of claim 1, wherein the memory further stores a paradigm logic library containing a plurality of testing paradigms, wherein the memory further stores a stimulus library containing a plurality of stimuli, wherein the act of executing a selected one of the stored evoked response testing protocols comprises:

(i) accessing a selected testing paradigm contained in the paradigm logic library stored in the memory, (ii) accessing stimuli specified by the selected testing paradigm contained in the stimulus library stored in the memory, (iii) calculating sequence and interstimulus delays between selected stimuli in accordance with the selected testing paradigm, and (iv) outputting a testing stream to the headset.

13. The method of claim 1, further comprising:

(a) detecting an artifact in data associated with manual inputs received from the test subject;

(b) accessing an epoch grouping of stimuli associated with the artifact; and (c) replaying the associated epoch grouping.

14. The method of claim 1, further comprising processing the recorded data based on a predetermined neurological diagnosis associated with the test subject.

15. The method of claim 14, wherein the act of processing the recorded data based on a predetermined neurological diagnosis associated with the test subject comprises refining a selected evoked response testing protocol.

16. A method of using an Evoked Response Potential (ERP) testing system to administer a test on a test subject, wherein the ERP testing system comprises a headset, the method comprising:

(a) positioning the headset on the head of the test subject, wherein the headset comprises:
  (i) a signal electrode,
  (ii) a reference electrode,
  (iii) a stimulus producer,
  (iv) a semi-rigid frame,
  (v) a control module contained within the semi-rigid frame, and
  (vi) a forehead frame configured to align with the eyebrows of the head, wherein aligning the forehead frame with the eyebrows results in proper placement of the plurality of electrodes;

(b) placing a handheld control box in a hand of the test subject, wherein the handheld control box further comprises:
  (i) a memory, wherein the memory stores a plurality of evoked response testing protocols including instructions for the stimulus producer, and
  (ii) a controller operably configured to actuate one of the plurality of evoked response testing protocols stored in the memory, wherein the controller is further configured to communicate a plurality of control administration parameters to the headset for performing an evoked response test;

(c) performing an ERP test, wherein the act of performing an ERP test comprises:
  (i) performing a self-test via the headset to verify good reception of an EEG signal,
  (ii) pausing the ERP test until a patient identification associated with the test subject is received by the headset and then automatically resuming,
  (iii) measuring a resting EEG result via the signal electrode and imposing a threshold delay if the resting EEG result is not below a threshold indicating a resting state,
  (iv) when the slope of the resting EEG result meets a criteria indicating a resting state, presenting a stimulus via the stimulus producer while measuring a stimulated EEG result, and
  (v) analyzing the stimulated EEG result via the signal electrode for artifacts, and imposing an artifact delay and re-measuring the stimulated EEG result if artifacts are present;

(d) placing the headset in communication with a computer and transferring an electronic medical record and the stimulated EEG result to the computer; and
(e) upon a successful data transfer, clearing the headset memory of the electronic medical record and the stimulated EEG result.

17. A method of using an Evoked Response Potential (ERP) testing system to administer a test on a human child, wherein the ERP testing system comprises a headset, the method comprising:
(a) positioning the headset on the head of the child, wherein the headset comprises:
(i) a plurality of flexible arms cantilevered to exert force upon a plurality of electrodes and place them in contact with the head,
(ii) the plurality of electrodes comprising a reference electrode, a signal electrode, and a plurality of fluid-filled bladders configured to reduce discomfort and provide uniform contact between the head and the plurality of electrodes,
(iii) a stimulus producer,
(iv) a semi-rigid frame with a left ear cup and a right ear cup, wherein the semi-rigid frame is curved such that. as the semi-rigid frame flexes as a result of increasing the distance between the left ear cup and the right ear cup, the orientation of the left ear cup and the right ear cup do not change with respect to the head,
(v) a control module contained within the semi-rigid frame; and
(vi) a forehead frame configured to align with the eyebrows of the head, wherein aligning the forehead frame with the eyebrows results in proper placement of the plurality of electrodes;
(b) placing a handheld control box in a hand of the child, wherein the handheld control box further comprises:
(i) a memory, wherein the memory stores a plurality of evoked response testing protocols including instructions for the stimulus producer, and
(ii) a controller operably configured to actuate one of the plurality of evoked response testing protocols stored in the memory, wherein the controller is further configured to communicate a plurality of control administration parameters to the headset for performing an evoked response test;
(c) performing an ERP test, wherein the act of performing an ERP test comprises executing a selected one of the stored evoked response testing protocols though the headset via the controller, wherein all of the functionality required to perform the selected one of the stored evoked response testing protocols is included in the headset and the handheld control box;
(d) receiving results of the ERP test, wherein the act of receiving results of the ERP test comprises receiving manual inputs from the child via the one or more buttons on the handheld control box during the act of performing an ERP test and receiving a stimulated EEG result via the plurality of electrodes; and
(e) recording the ERP test results in the memory.

18. The method of claim 1, wherein the headset further comprises a control box, wherein positioning the headset further comprises:
(a) using one or more physical indicators on the semi-rigid frame to properly position the headset;
(b) performing a self test to check electrode continuity; and
(c) displaying a detailed explanation of the self test results via a display on the control box.

19. The method of claim 18, further comprising:
(a) in response to a self test pass, locating a machine readable patient identification;
(b) interpreting the machine readable patient identification via an identification input on the control box; and
(c) verifying the machine readable patient identification and associating it with data recorded in the memory.

20. The method of claim 16 wherein the headset is configured to be able to produce a plurality of stimuli including at least one of the following:
(a) a click characterized by a narrow band spike;
(b) a burst characterized by a broadband short duration;
(c) a chirp characterized by a single frequency half-cycle carrier;
(d) a steady-state tone characterized by a single frequency constant amplitude;
(e) a master characterized by a single frequency continuous cycle;
(f) a phoneme characterized by a single-phoneme speech sound; or
(g) a spoken word; and
wherein the headset is configured to be able to produce the plurality of stimuli in a plurality of sequences including at least one of the following:
(i) repeating a single stimuli;
(ii) a single tone with a long duration;
(iii) multiple stimuli with each repeated an equal number of times;
(iv) a pair of stimuli, presented with minimal interstimulus delay, which either match or do not match;
(v) a single standard stimuli with one or more deviant stimuli;
(vi) a constant volume with varying frequency;
(vii) a constant frequency with varying volume;
(viii) a constant tone with varying duration; or
(ix) a user defined sequence presentation, volume, tone, and time warp.

* * * * *